(12) United States Patent
Sawhney et al.

(10) Patent No.: US 9,370,485 B2
(45) Date of Patent: *Jun. 21, 2016

(54) HYDROGEL POLYMERIC COMPOSITIONS AND METHODS

(71) Applicant: Incept, LLC, Lexington, MA (US)

(72) Inventors: Amarpreet S. Sawhney, Lexington, MA (US); William H. Ransone, II, Waltham, MA (US)

(73) Assignee: Incept, LLC, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/470,081

(22) Filed: Aug. 27, 2014

(65) Prior Publication Data

US 2014/0363498 A1    Dec. 11, 2014

Related U.S. Application Data

(63) Continuation of application No. 12/485,192, filed on Jun. 16, 2009, which is a continuation of application No. 11/825,848, filed on Jul. 9, 2007, now Pat. No. 9,125,807.

(51) Int. Cl.
| | | |
|---|---|---|
| A61K 47/10 | (2006.01) |
| A61K 9/00 | (2006.01) |
| A61K 31/196 | (2006.01) |
| A61K 31/405 | (2006.01) |
| A61K 31/4422 | (2006.01) |
| A61K 31/4458 | (2006.01) |
| A61K 31/496 | (2006.01) |
| A61K 31/573 | (2006.01) |
| A61K 31/58 | (2006.01) |

(52) U.S. Cl.
CPC ............ *A61K 9/0051* (2013.01); *A61K 31/196* (2013.01); *A61K 31/405* (2013.01); *A61K 31/4422* (2013.01); *A61K 31/4458* (2013.01); *A61K 31/496* (2013.01); *A61K 31/573* (2013.01); *A61K 31/58* (2013.01); *A61K 47/10* (2013.01)

(58) Field of Classification Search
None
See application file for complete search history.

(56) References Cited

U.S. PATENT DOCUMENTS

| | | |
|---|---|---|
| 3,949,750 A | 4/1976 | Freeman |
| 3,995,635 A | 12/1976 | Higuchi et al. |

(Continued)

FOREIGN PATENT DOCUMENTS

| | | |
|---|---|---|
| EP | 1704878 | 9/2006 |
| EP | 1967220 | 9/2008 |

(Continued)

OTHER PUBLICATIONS

S Cohen, E Lobel, A Trevgoda, Y Peled. "A novel in situ-forming ophthalmic drug delivery system from alginates undergoing gelation in the eye." Journal of Controlled Release, vol. 44, 1997, pp. 201-208.*

Z Liu, J Li, S Nie, H Liu, P Ding, W Pan. "Study of an alginate/HPMC-based in situ gelling ophthalmic delivery system for gatifloxacin." International Journal of Pharmaceutics, vol. 315, 2006, pp. 12-17.*

B Srividya, RM Cardoza, PD Amin. "Sustained ophthalmic delivery of ofloxacin from a pH triggered in situ gelling system." Journal of Controlled Release, vol. 73, 2001, pp. 205-211.*

(Continued)

*Primary Examiner* — Isaac Shomer
(74) *Attorney, Agent, or Firm* — Dardi & Herbert, PLLC; Curtis B. Herbert

(57) ABSTRACT

Some aspects of this disclosure relate to a method of treating an ophthalmic disease affecting an eye of a patient comprising forming a covalently-crosslinked hydrogel in situ at a peri-ocular, intra-ocular, or intra-vitreal site for controlled release of a therapeutic agent.

21 Claims, 14 Drawing Sheets

(56) References Cited

U.S. PATENT DOCUMENTS

| | | | |
|---|---|---|---|
| 4,424,311 | A | 1/1984 | Nagaoka et al. |
| 4,693,887 | A | 9/1987 | Shah |
| 4,740,534 | A | 4/1988 | Matsuda et al. |
| 4,741,872 | A | 5/1988 | DeLuca et al. |
| 4,760,131 | A | 7/1988 | Sundsmo et al. |
| 4,803,075 | A | 2/1989 | Wallace et al. |
| 4,826,945 | A | 5/1989 | Cohn et al. |
| 4,853,224 | A | 8/1989 | Wong |
| 4,938,763 | A | 7/1990 | Dunn et al. |
| 4,952,581 | A | 8/1990 | Bio et al. |
| 4,979,959 | A | 12/1990 | Guire |
| 5,041,292 | A | 8/1991 | Feijen |
| 5,100,992 | A | 3/1992 | Cohn et al. |
| 5,122,614 | A | 6/1992 | Zalipsky |
| 5,160,745 | A | 11/1992 | DeLuca et al. |
| 5,162,430 | A | 11/1992 | Rhee et al. |
| 5,227,372 | A | 7/1993 | Folkman |
| 5,266,325 | A | 11/1993 | Kuzma et al. |
| 5,278,202 | A | 1/1994 | Dunn et al. |
| 5,296,228 | A | 3/1994 | Chang et al. |
| 5,304,595 | A | 4/1994 | Rhee et al. |
| 5,306,500 | A | 4/1994 | Rhee et al. |
| 5,324,775 | A | 6/1994 | Rhee et al. |
| 5,380,536 | A | 1/1995 | Hubbell et al. |
| 5,410,016 | A | 4/1995 | Hubbell et al. |
| 5,446,090 | A | 8/1995 | Harris |
| 5,446,091 | A | 8/1995 | Rhee et al. |
| 5,462,990 | A | 10/1995 | Hubbell et al. |
| 5,480,914 | A | 1/1996 | Meadows |
| 5,510,418 | A | 4/1996 | Rhee et al. |
| 5,514,379 | A | 5/1996 | Weissleder et al. |
| 5,527,856 | A | 6/1996 | Rhee et al. |
| 5,529,914 | A | 6/1996 | Hubbell et al. |
| 5,543,441 | A | 8/1996 | Rhee et al. |
| 5,550,187 | A | 8/1996 | Rhee et al. |
| 5,550,188 | A | 8/1996 | Rhee et al. |
| 5,565,215 | A | 10/1996 | Gref et al. |
| 5,565,519 | A | 10/1996 | Rhee et al. |
| 5,567,435 | A | 10/1996 | Hubbell et al. |
| 5,567,440 | A | 10/1996 | Hubbell et al. |
| 5,573,934 | A | 11/1996 | Hubbell et al. |
| 5,578,638 | A | 11/1996 | Brazzell et al. |
| 5,583,114 | A | 12/1996 | Barrows et al. |
| 5,587,175 | A | 12/1996 | Viegas et al. |
| 5,618,563 | A | 4/1997 | Berde et al. |
| 5,626,863 | A | 5/1997 | Hubbell et al. |
| 5,627,233 | A | 5/1997 | Hubbell et al. |
| 5,629,922 | A * | 5/1997 | Moodera .......... B82Y 25/00 257/421 |
| 5,650,173 | A | 7/1997 | Ramstack et al. |
| 5,660,849 | A | 8/1997 | Polson et al. |
| 5,662,712 | A | 9/1997 | Pathak et al. |
| 5,665,840 | A | 9/1997 | Pohlmann et al. |
| 5,705,194 | A | 1/1998 | Wong et al. |
| 5,717,614 | A | 2/1998 | Shah et al. |
| 5,731,005 | A | 3/1998 | Ottoboni et al. |
| 5,741,323 | A | 4/1998 | Pathak et al. |
| 5,744,545 | A | 4/1998 | Rhee et al. |
| 5,752,974 | A | 5/1998 | Rhee et al. |
| 5,776,445 | A | 7/1998 | Cohen et al. |
| 5,800,373 | A | 9/1998 | Hubbell et al. |
| 5,801,033 | A | 9/1998 | Hubbell et al. |
| 5,820,882 | A | 10/1998 | Hubbell et al. |
| 5,834,274 | A | 11/1998 | Hubbell et al. |
| 5,837,226 | A | 11/1998 | Jungherr et al. |
| 5,843,743 | A | 12/1998 | Hubbell et al. |
| 5,844,016 | A | 12/1998 | Sawhney et al. |
| 5,849,035 | A | 12/1998 | Pathak et al. |
| 5,849,839 | A | 12/1998 | Hubbell et al. |
| 5,858,746 | A | 1/1999 | Hubbell et al. |
| 5,874,500 | A | 2/1999 | Rhee et al. |
| 5,879,688 | A | 3/1999 | Coury et al. |
| 5,888,493 | A | 3/1999 | Sawaya |
| 5,936,035 | A | 8/1999 | Rhee et al. |
| 5,981,607 | A | 11/1999 | Ding et al. |
| 5,986,043 | A | 11/1999 | Hubbell et al. |
| 6,051,638 | A | 4/2000 | Rhee et al. |
| 6,060,582 | A | 5/2000 | Hubbell et al. |
| 6,071,875 | A | 6/2000 | Clark et al. |
| 6,083,524 | A | 7/2000 | Sawhney et al. |
| 6,110,484 | A | 8/2000 | Sierra |
| 6,121,341 | A | 9/2000 | Sawhney et al. |
| 6,123,667 | A | 9/2000 | Poff et al. |
| 6,132,986 | A | 10/2000 | Pathak et al. |
| 6,149,931 | A | 11/2000 | Schwartz et al. |
| 6,152,943 | A | 11/2000 | Sawhney |
| 6,153,211 | A | 11/2000 | Hubbell et al. |
| 6,154,671 | A | 11/2000 | Parel et al. |
| 6,156,345 | A | 12/2000 | Chudzik et al. |
| 6,156,531 | A | 12/2000 | Pathak et al. |
| 6,162,241 | A | 12/2000 | Coury et al. |
| 6,165,201 | A | 12/2000 | Sawhney et al. |
| 6,165,489 | A | 12/2000 | Berg et al. |
| 6,166,130 | A | 12/2000 | Rhee et al. |
| 6,171,600 | B1 | 1/2001 | Dahms |
| 6,176,871 | B1 | 1/2001 | Pathak et al. |
| 6,177,095 | B1 | 1/2001 | Sawhney et al. |
| 6,177,514 | B1 | 1/2001 | Pathak et al. |
| 6,179,862 | B1 | 1/2001 | Sawhney |
| 6,196,993 | B1 | 3/2001 | Cohan et al. |
| 6,201,065 | B1 | 3/2001 | Pathak et al. |
| 6,214,996 | B1 | 4/2001 | Harris |
| 6,217,896 | B1 | 4/2001 | Benjamin |
| 6,231,892 | B1 | 5/2001 | Hubbell et al. |
| 6,242,442 | B1 | 6/2001 | Dean et al. |
| 6,258,870 | B1 | 7/2001 | Hubbell et al. |
| 6,261,544 | B1 | 7/2001 | Coury et al. |
| 6,277,394 | B1 | 8/2001 | Sierra |
| 6,297,240 | B1 | 10/2001 | Embleton |
| 6,306,922 | B1 | 10/2001 | Hubbell et al. |
| 6,312,725 | B1 | 11/2001 | Wallace et al. |
| 6,316,441 | B1 | 11/2001 | Dean et al. |
| 6,319,240 | B1 | 11/2001 | Beck |
| 6,322,593 | B1 | 11/2001 | Pathak et al. |
| 6,335,335 | B2 | 1/2002 | Higashiyama et al. |
| 6,371,975 | B2 | 4/2002 | Cruise et al. |
| 6,379,373 | B1 | 4/2002 | Sawhney et al. |
| 6,387,977 | B1 | 5/2002 | Sawhney et al. |
| 6,410,045 | B1 | 6/2002 | Schultz et al. |
| 6,410,645 | B1 | 6/2002 | Pathak et al. |
| 6,413,539 | B1 | 7/2002 | Shalaby |
| 6,416,740 | B1 | 7/2002 | Unger |
| 6,458,889 | B1 | 10/2002 | Trollsas et al. |
| 6,465,001 | B1 | 10/2002 | Hubbell et al. |
| 6,479,079 | B1 | 11/2002 | Pathak et al. |
| 6,495,127 | B1 | 12/2002 | Wallace et al. |
| 6,514,534 | B1 | 2/2003 | Sawhney |
| 6,528,107 | B2 | 3/2003 | Chinn et al. |
| 6,534,591 | B2 | 3/2003 | Rhee et al. |
| 6,539,251 | B2 | 3/2003 | Beck et al. |
| 6,566,406 | B1 | 5/2003 | Pathak et al. |
| 6,579,519 | B2 | 6/2003 | Maitra et al. |
| 6,596,471 | B2 | 7/2003 | Pathak et al. |
| 6,602,952 | B1 | 8/2003 | Bentley et al. |
| 6,602,975 | B2 | 8/2003 | Hubbell et al. |
| 6,605,294 | B2 | 8/2003 | Sawhney |
| 6,610,033 | B1 | 8/2003 | Melanson et al. |
| 6,624,245 | B2 | 9/2003 | Wallace et al. |
| 6,632,446 | B1 | 10/2003 | Hubbell et al. |
| 6,632,457 | B1 | 10/2003 | Sawhney |
| 6,639,014 | B2 | 10/2003 | Pathak et al. |
| 6,656,200 | B2 | 12/2003 | Li et al. |
| 6,673,093 | B1 | 1/2004 | Sawhney |
| 6,689,148 | B2 | 2/2004 | Sawhney et al. |
| 6,703,047 | B2 | 3/2004 | Sawhney et al. |
| 6,709,668 | B2 | 3/2004 | Won et al. |
| 6,710,126 | B1 | 3/2004 | Hirt et al. |
| 6,747,090 | B2 | 6/2004 | DeGroot et al. |
| 6,777,000 | B2 | 8/2004 | Ni et al. |
| 6,818,018 | B1 | 11/2004 | Sawhney |
| 6,833,408 | B2 | 12/2004 | Sehl et al. |
| 6,861,065 | B2 | 3/2005 | Hodd et al. |
| 6,887,974 | B2 | 5/2005 | Pathak |
| 6,905,700 | B2 | 6/2005 | Won et al. |

(56) References Cited

U.S. PATENT DOCUMENTS

| | | | |
|---|---|---|---|
| 6,911,227 B2 | 6/2005 | Hubbell et al. |
| 6,911,496 B2 | 6/2005 | Rhee et al. |
| 6,916,857 B2 | 7/2005 | Won et al. |
| 6,923,986 B2 | 8/2005 | Pathak et al. |
| 6,936,005 B2 | 8/2005 | Poff et al. |
| 6,958,212 B1 | 10/2005 | Hubbell et al. |
| 6,962,979 B1 | 11/2005 | Rhee |
| 7,009,034 B2 | 3/2006 | Pathak et al. |
| 7,025,990 B2 | 4/2006 | Sawhney |
| 7,057,019 B2 | 6/2006 | Pathak |
| 7,060,297 B2 | 6/2006 | Karakelle et al. |
| 7,129,210 B2 | 10/2006 | Lowinger et al. |
| 7,141,248 B2 | 11/2006 | Hodd et al. |
| 7,153,519 B2 | 12/2006 | Hubbell et al. |
| 7,211,651 B2 | 5/2007 | Pathak |
| 7,220,270 B2 | 5/2007 | Sawhney et al. |
| RE39,713 E | 7/2007 | Sawhney et al. |
| 7,238,364 B2 | 7/2007 | Sawhney et al. |
| 7,589,057 B2 | 9/2009 | Chang et al. |
| 9,125,807 B2 * | 9/2015 | Sawhney ............ A61K 9/0051 |
| 2002/0026176 A1 | 2/2002 | Varner et al. |
| 2002/0064513 A1 | 5/2002 | Maitra et al. |
| 2002/0071874 A1 | 6/2002 | Olejnik et al. |
| 2002/0082636 A1 | 6/2002 | Sawhney et al. |
| 2002/0114778 A1 | 8/2002 | Xia et al. |
| 2002/0119941 A1 | 8/2002 | Ni et al. |
| 2002/0197300 A1 | 12/2002 | Schultz et al. |
| 2003/0012734 A1 | 1/2003 | Pathak et al. |
| 2003/0017199 A1 | 1/2003 | Woodward et al. |
| 2003/0147849 A1 | 8/2003 | Warne et al. |
| 2003/0171320 A1 | 9/2003 | Guyer |
| 2003/0175324 A1 | 9/2003 | Robinson et al. |
| 2003/0185892 A1 | 10/2003 | Bell et al. |
| 2003/0191426 A1 | 10/2003 | Lerner et al. |
| 2004/0009205 A1 | 1/2004 | Sawhney |
| 2004/0037889 A1 | 2/2004 | Richeal et al. |
| 2004/0076602 A1 | 4/2004 | Harris |
| 2004/0086479 A1 | 5/2004 | Grinstaff et al. |
| 2004/0131582 A1 | 7/2004 | Grinstaff et al. |
| 2004/0175410 A1 | 9/2004 | Ashton et al. |
| 2004/0230183 A1 | 11/2004 | Breegi et al. |
| 2005/0043220 A1 * | 2/2005 | Guyer ................ C12N 15/1136 514/8.1 |
| 2005/0080445 A1 | 4/2005 | Sawhney et al. |
| 2005/0169882 A1 | 8/2005 | Lowe et al. |
| 2005/0171212 A1 | 8/2005 | Gierhart |
| 2005/0232872 A1 | 10/2005 | Deaver et al. |
| 2005/0244464 A1 | 11/2005 | Hughes |
| 2005/0256065 A1 | 11/2005 | Harris et al. |
| 2005/0277864 A1 | 12/2005 | Haffner et al. |
| 2005/0288197 A1 | 12/2005 | Horn |
| 2006/0002963 A1 | 1/2006 | Rabinovich-Guilatt et al. |
| 2006/0013859 A1 | 1/2006 | Yamada et al. |
| 2006/0039479 A1 | 2/2006 | Francois et al. |
| 2006/0039979 A1 | 2/2006 | Yamada et al. |
| 2006/0079599 A1 | 4/2006 | Arthur |
| 2006/0100288 A1 | 5/2006 | Bague et al. |
| 2006/0147409 A1 | 7/2006 | Pathak et al. |
| 2006/0177481 A1 | 8/2006 | Sawhney |
| 2006/0182771 A1 | 8/2006 | Dor et al. |
| 2006/0182781 A1 | 8/2006 | Hughes et al. |
| 2006/0193899 A1 | 8/2006 | Sawhney |
| 2006/0258698 A1 | 11/2006 | Mudumba et al. |
| 2006/0286173 A1 | 12/2006 | Yamada et al. |
| 2007/0195261 A1 | 8/2007 | Vogt et al. |
| 2007/0197776 A1 | 8/2007 | Pathak |
| 2007/0224246 A1 | 9/2007 | Hughes et al. |
| 2007/0231366 A1 | 10/2007 | Sawhney et al. |
| 2007/0233240 A1 | 10/2007 | Frank et al. |
| 2007/0248567 A1 | 10/2007 | Pathak et al. |
| 2007/0282366 A1 | 12/2007 | Khosravi et al. |
| 2008/0038317 A1 | 2/2008 | Chang et al. |
| 2008/0114092 A1 | 5/2008 | Sawhney |
| 2008/0220047 A1 | 9/2008 | Sawhney et al. |
| 2008/0268020 A1 | 10/2008 | Philips et al. |
| 2009/0215923 A1 | 8/2009 | Carnahan et al. |
| 2009/0227981 A1 | 9/2009 | Bennett |
| 2010/0104654 A1 | 4/2010 | Robinson et al. |
| 2010/0158980 A1 | 6/2010 | Kopczynski et al. |

FOREIGN PATENT DOCUMENTS

| | | |
|---|---|---|
| WO | 9719973 | 6/1997 |
| WO | 9722371 | 6/1997 |
| WO | 9812274 | 3/1998 |
| WO | 9835631 | 3/1998 |
| WO | 0007603 | 2/2000 |
| WO | 2004028404 | 4/2004 |
| WO | 2006026325 | 3/2006 |
| WO | 2006031358 | 3/2006 |
| WO | 2006031388 | 3/2006 |
| WO | 2006096586 | 9/2006 |
| WO | 2007001926 | 1/2007 |
| WO | 2007005249 | 1/2007 |

OTHER PUBLICATIONS

United States Court of Appeals for the Federal Circuit. *Magsil Corporation and Massachusetts Institute of Technology v. Hitachi Global Storage Technologies, Inc., Hitachi America, Ltd., Hitachi Data Systems Corporation, and Shenzhen Excelstor Technology Ltd.* Case 2011-1221, Aug. 14, 2012, pp. 1-14.*

D Gulsen, A Chauhan. "Ophthalmic Drug Delivery through Contact Lenses." Investigative Ophthalmology and Visual Science, vol. 45 No. 7, Jul. 2004, pp. 2342-2347.*

Al-Aswad "Another Role for Avastin? Neocasculat Glaucoma" Review of Ophthalmology Online, http://www.revophth.com/content/d/cover_focus/i/1304/c/250941 (accessed Oct. 22, 2012), Jun. 13, 2006, 5 pages.

Dunn et al., "Evaluation of the SprayGel adhesion barrier in the rat cecum abrasion and rabbit uterine horn adhesion models", Fertility and Sterility, 75(2): 411-416 (Feb. 2001).

Dunn et al., "Rat (Abdominal) & Rat (Pelvic) Studies", Efficacy Preclinical Studies brochure.

Ferland et al., "Porcine (Pelvic) Efficacy Studies", Efficacy Preclinical Studies brochure.

Gulsen et al., "Ophthalmic Drug Delivery Through Contact Lenses", Investigative Ophthalmology & Visual Science, vol. 45(7), (Jul. 2004).

Internet Archive, Search results for (http://chemistry2.csudh.edu/rpedarvis/AmAcSeqSyn.html., Accessed Mar. 23, 2009.

Jain et al. "Lessons from phase III clinical trials on anti-VEGF therapy for cancer" Nature Clinical Practice Oncology, vol. 3 No. 1, Jan. 2006, pp. 24-40.

Neises et al., "Esterification of Carboxylic Acids with Dicyclohexylcarbodiimide/4-Dimethylaminopyridime: tert-Butyl Ethyl Fumarate", Organic Syntheses, Coll. vol. 7, p. 93 (1990), vol. 63, p. 183 (1985).

Office Action dated Aug. 5, 2009.

Peptide Sequencing and Synthesis "Chemistry 240 Summer 2001.", May 8, 2003 (as of Internet Archive). Http://chemistry2csudh.edu/rpendarvis/Am/AcSeqSyn.html.

Sawhney et al., "Rabbit (Pericardial) Adhesion Study", Efficacy Preclinical Studies brochure.

Srividya et al., "Sustained Ophthalmic Delivery of Ofloxacin from a pH Triggered In Situ Gelling System", Journal of Controlled Release, 73:205-211 (2001).

Communications from U.S. Appl. No. 12/704,692 dated from Dec. 15, 2011 to Mar. 15, 2012.

Supplementary European Search Report from corresponding EP Patent Application No. 08754416.9 dated Jul. 9, 2012 (5 pages).

Yasukawa et al., "Biodegradable Scleral Plugs for Vitreoretinal Drug Delivery", Advanced Drug Delivery Review, vol. 52:25-36 (2001).

* cited by examiner

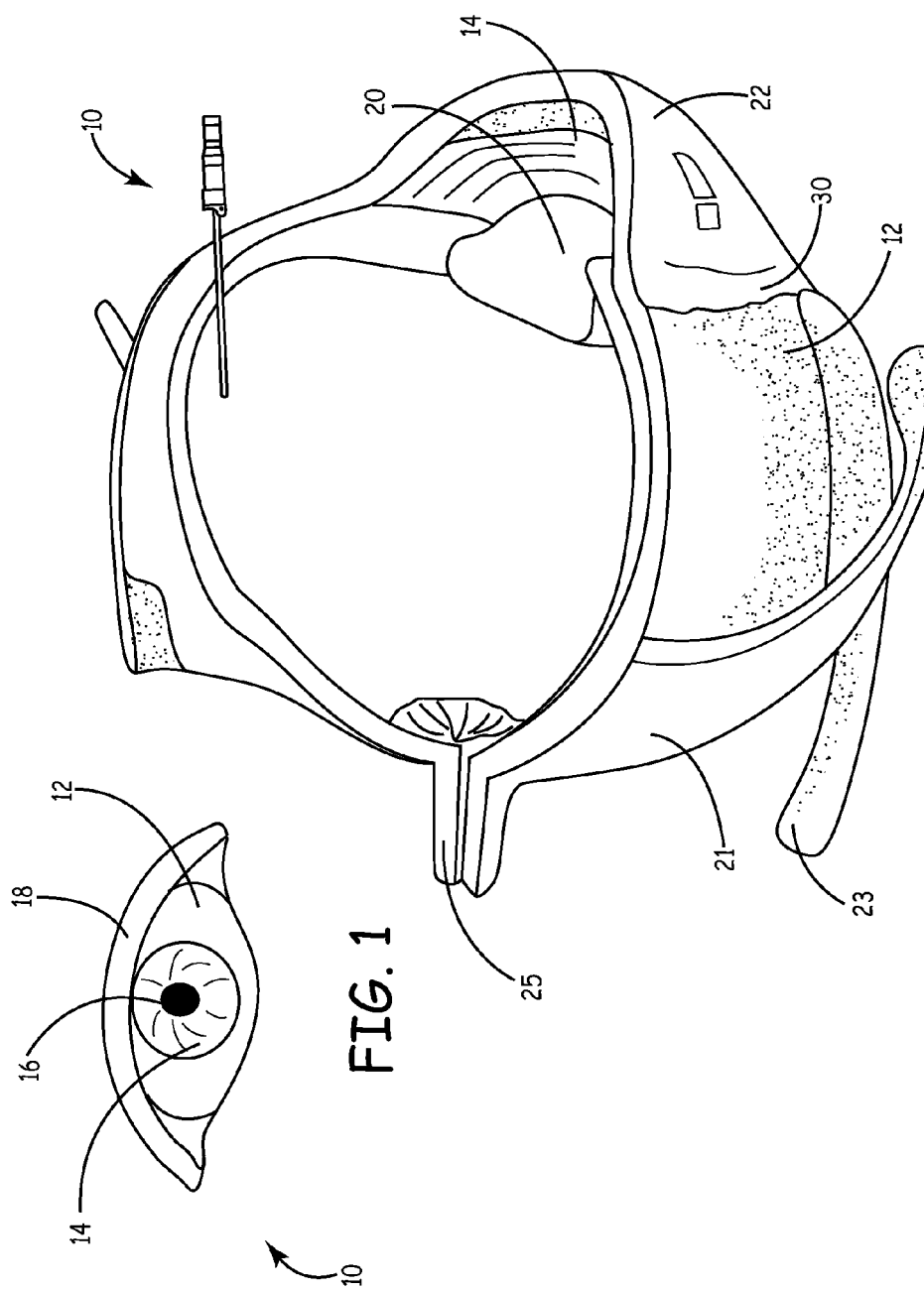

HYDROGEL POLYMERIC COMPOSITIONS AND METHODS

CROSS-REFERENCE TO RELATED APPLICATIONS

This patent application is a continuation of U.S. patent application Ser. No. 12/485,192 filed Jun. 16, 2009 which is a continuation of U.S. patent application Ser. No. 11/825,848 filed Jul. 9, 2007, which are hereby incorporated by reference herein.

TECHNICAL FIELD

The technical field, in general, relates to synthetic polymeric resins that are hydrogel compositions, as applied to certain medical conditions.

BACKGROUND

Age-related macular degeneration (AMD), diabetic retinopathy, diabetic macular edema (DME) posterior uveitis, choroidal neovascularization (CNV) and cystoid macular edema (CME) are sight-threatening back-of-the-eye diseases. Age related macular degeneration and diabetic retinopathy are significant causes of visual impairment in the United States and elsewhere; these conditions are generally caused by angiogenesis (unwanted blood-vessel growth in the eye) that damages the retina and ultimately can cause blindness. Posterior uveitis is a chronic inflammatory condition that causes about ten percent of the blindness in the United States.

SUMMARY

One invention disclosed herein is a crosslinked hydrogel formed in-situ that releases a therapeutic agent that can be used to treat back-of-the eye diseases. In this embodiment, aqueous polymeric precursors are combined ex vivo in flowable concentrations/viscosities with a drug and injected intravitreally or via subconjunctival routes through a small gauge needle into the eye, where the precursors form a crosslinked hydrogel that releases the drug over time. The hydrogel may be formulated to adhere to a tissue in or around the eye to enhance drug release effects and stability, to degrade to biocompatible components without causing inflammation, and to crosslink in place. A shape-stable hydrogel thus formed can effectively deliver the drug and advantageously have a well-controlled size, shape, and surface area. A small gauge needle or blunt tip cannula for sub-Tenon's injections may be used to inject the materials since soluble or flowable precursors may be used instead of an already-formed material.

A biocompatible material may be created for eye treatments, one that causes minimal inflammation. The hydrogels are made using biocompatible precursors, contain high proportions of water, and make biocompatible degradation products. The materials may thus be soft, hydrophilic, and conforming to space where they are made, without hard edges, corners, or sharp surfaces.

Biodegradable materials can also be made that are effectively self-removing or, if removed, leave only portions that are self-removing. Some embodiments are implants made with a soft, flexible biomaterials crosslinked for strength so the implants they can be pulled out or otherwise evacuated though a small opening in case their retrieval is needed.

BRIEF DESCRIPTION OF THE FIGURES

FIG. 1 depicts anatomical features of an eye from a frontal view;

FIG. 2 is a partially cut-away perspective view of an eye;

DETAILED DESCRIPTION

Figure 3:
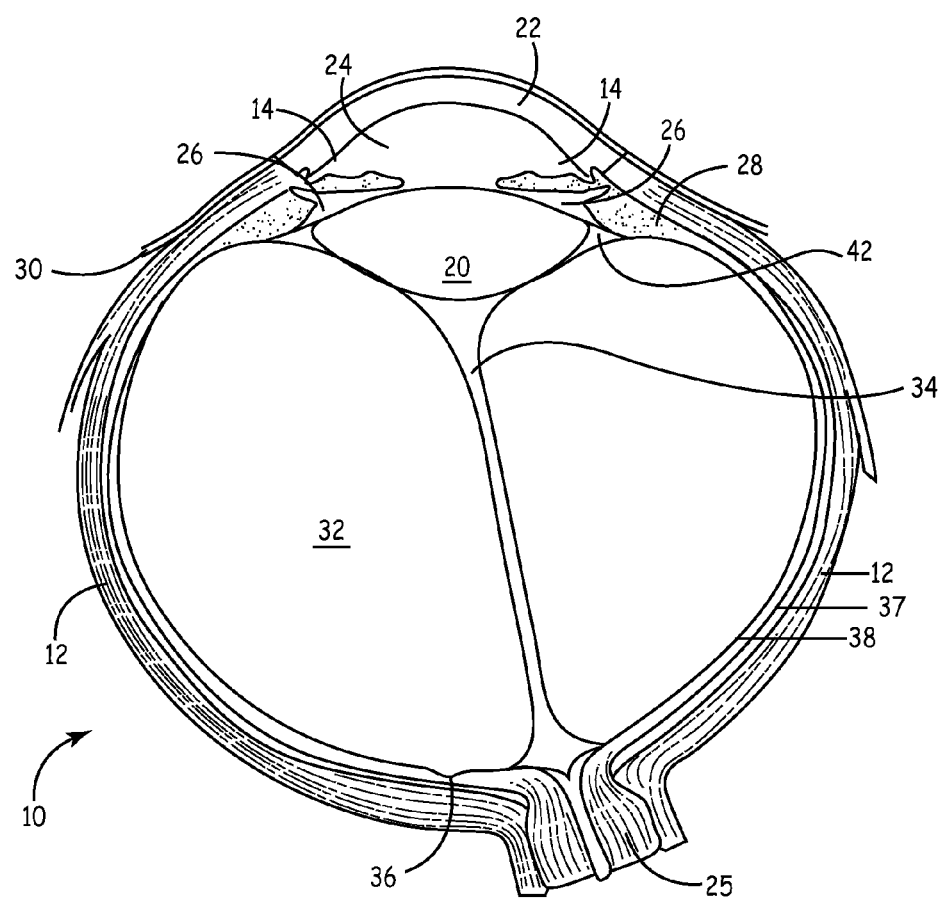
FIG. 3 is a cross-sectional view of an eye.

Locally formed hydrogels made in-situ from precursors in aqueous solution can serve as depots of drugs or other therapeutic agents for ocular drug delivery. These depots can be formed as needed, e.g., topically on the surface of the eye, trans-scleral in and/or between the conjunctival and scleral tissues, injected intraocularly, or formed periocularly.

There are a variety of serious eye diseases that need treatment with a drug regimen. Described herein are hydrogels that can be formed in situ on a tissue to deliver drugs. In situ refers to forming a material at its intended site of use. Thus a hydrogel may be formed in situ in a patient at the site wherein the hydrogel is intended to be used, e.g., as a drug depot for controlled release.

The hydrogel is, in one embodiment, formed from precursors having functional groups that form covalent crosslinks to crosslink the hydrogels and thereby form the hydrogel. The hydrogel delivers drugs to the eye. Some embodiments use highly flowable precursors that gel slowly enough to be forced through a very small bore cannula or needle to essentially cross-link only after injection, but nonetheless gel quickly enough so that they do not migrate back through the track of the incision. This gel then swells minimally after crosslinking. The gel degrades in the physiological fluid in or around the eye without causing inflammation by degrading into parts that are biocompatible and not acidic. The hydrogel also has enough mechanical strength so that it can be recovered by means of either manual or mechanical irrigation/aspiration techniques if necessary. Moreover, in some embodiments the gel adheres to the tissue.

In general, precursors may be combined as described herein at a site in or near an eye to make a covalently-crosslinked hydrogel that comprises a therapeutic agent that is released into the eye to treat an opthalmic disease over a suitable period of time. The hydrogel may be low-swelling, as measurable by the hydrogel having a weight increasing no more than about 10% or about 50% upon exposure to a physiological solution for twenty-four hours relative to a weight of the hydrogel at the time of formation; artisans will immediately appreciate that all the ranges and values within the explicitly stated ranges are contemplated. The hydrogel also may be water-degradable, as measurable by the hydrogel being dissolvable in vitro in an excess of water by degradation of water-degradable groups in the hydrogel. A composition with the precursors mixed therein can be introduced through a small-gauge needle provided that the composition has a suitable viscosity, which in turn depends on precursor properties, concentrations, and chemistry. Further, the hydrogels' mechanical strengths and reaction time are adjusted though control of the precursors and functional groups. The precursors and hydrogels may have various features that can be mixed-and-matched as guided by the considerations for making an effective device; the following sections describe some of these features.

Precursor Materials

The precursors can be triggered to react to form a crosslinked hydrogel. In general, the precursors are polymerizable and include crosslinkers that are often, but not always, polymerizable precursors. Polymerizable precursors are thus precursors that have functional groups that react with each other to form polymers made of repeating units.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference to the extent it does not contradict what is explicitly disclosed herein.

Some precursors react by a chain growth-step system. Chain growth polymers are defined as polymers formed by the reaction of monomers or macromonomers with a reactive center. A reactive center is a particular location within a chemical compound that is the center of a reaction in which the chemical is involved. In chain-growth polymer chemistry, this is also the point of propagation for a growing chain. The reactive center is commonly radical, anionic, or cationic in nature, but can also take other forms. Chain growth-step systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is an organic molecule formed by combining many smaller molecules (monomers) in a regular pattern, and includes those formed from at least two monomers and also oligomers, which is a term herein referring to polymers having less than about 20 monomeric repeat units. A small molecule generally refers to a molecule that is less than about 2000 Daltons.

The precursors must thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which are hereby incorporated by reference to the extent they do not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two monomers can serve as crosslinkers since each monomer can participate in the formation of a different growing polymer chain. In the case of monomers with a reactive center, each monomer effectively has one functional group for reacting with other precursors. In the case of functional groups without a reactive center, among others, crosslinking requires three or more such functional groups on a precursor. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. Thus some precursors have functional groups for participating in polymer and/or crosslink formation but are free of polymerizable reactive centers or are free of radical and/or anionic and/or cationic reactive centers, or have only some combination of the same. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and water soluble portions, e.g., a core. A core refers to a contiguous portion of a molecule that is generally at least about 80% of the molecule by weight, sometimes with arms that extend from the core, with the arms having a functional group, which is often at the terminus of the branch. A water soluble portion is a water soluble molecule or polymer that is joined to a hydrophobic polymer. The water soluble precursor or precursor portion preferably has a solubility of at least 1 g/100 mL in an aqueous solution. A water soluble portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic.

A precursor may also be a macromolecule, which is a molecule having a molecular weight in the range of a few thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference to the extent it does not contradict what is explicitly disclosed. These monomers are characterized by having at least two polymerizable groups, separated by at least one degradable region.

Synthetic precursors may be used. Synthetic refers to a molecule not found in nature or not normally found in a human. Some synthetic polymers are free of amino acids or free of amino acid sequences that occur in nature. Some synthetic molecules are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be re-acted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH. In contrast, fibrin glues, which rely on polymerization of fibrinogen to form fibrin, have a limited range of mechanical properties, a limited range of degradability, and are not generally suited to many of the ophthalmic therapeutic applications that are available when hydrogels as described herein are formulated.

Precursors may be made with a hydrophobic portion. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, nonfibrin (ogen), non-hyaluronic acid, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources.

Peptides may be used as precursors. In general, peptides with less than about 10 residues are preferred, although larger sequences (e.g., proteins) may be used. Artisans will immediately appreciate that every range and value within these explicit bounds is included, e.g. 1-10, 2-9. 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide) refers to a polymer with a repeat group (CH2CH2O)n, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough CH2CH2O groups to total at least 1000 MW. As is customary terminology in these arts, a polyethylene glycol polymer does not necessarily terminate in a hydroxyl group.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Functional Groups

The precursors have functional groups that react with each other to form the material in situ. The functional groups generally have reactive centers for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. No. 5,410,016, or 6,149,931, each of which are hereby incorporated by reference to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michaels addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. The sulfonic acid salt on the succinimide ring does not alter the reactivity of NHS group with the primary amines. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7).

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly(ethylene glycol) can be used.

An arm on a hydrogel precursor refers to a linear chain of chemical groups that connect a crosslinkable functional group to polymer a core. Some embodiments are precursors with between 3 and 300 arms; artisans will immediately appreciate that all the ranges and values within the explicitly stated ranges are contemplated, e.g., 4 to 16, 8 to 100, or at least 6 arms. Precursors may be dendrimers, e.g., as in Patent Application Pub. No's. US20040086479, US20040131582, WO07005249, WO07001926, WO06031358, or the U.S. counterparts thereof; dendrimers may also be useful as multifunctional precursors, e.g., as in U.S. Patent Pub. No's. US20040131582, US20040086479 and PCT Applications No's WO06031388 and WO06031388; all of which US and PCT applications are hereby incorporated by reference to the extent they do not contradict what is explicitly disclosed herein. Dendrimers are highly ordered possess high surface area to volume ratios, and exhibit numerous end groups for potential functionalization. Some dendrimers are regularly ordered, meaning that each arm has an identical structure. Some dendrimers have arms with a plurality of serial branches meaning that a polymer branches into at least two arms that each branch into at least two more arms. Consequently, dendrimers tend to display low polydispersity indexes, low viscosities, and high solubility and miscibility. Some embodiments are directed to dendrimers with a relatively high molecular weight used with a relatively lower molecular weight multifunctional precursor, with suitable functional groups on the precursors. Other embodiments are directed to using dendrimers functionalized with electrophiles and/or nucleophiles. In some embodiments, the dendrimers serve as precursors with a relatively lower molecular weight (e.g., less than about half, less than about one-third) than another crosslinking precursor, e.g., with a dendrimer being between about 600 and about 3000 Da and a multifunctional precursor being between about 2000 to about 5000 Da. In some embodiments, the precursor is a hydrophilic dendrimer, e.g., comprising PEG. In some embodiments, each dendrimer arm, or at least half of the arms, terminates in a functional group for reaction with functional groups on other precursors. In some embodiments, dendrimer precursors of at least about 10,000 molecular weight are reacted with small precursors that crosslink the dendrimers, with the small precursors having a molecular weight of less than about 1000. In some embodiments, at least about 90% by number of the arms of the dendrimers are reacted to form links to the hydrogel; in other embodiments, less than about 25% by number of the arms are reacted so as to increase the mobility of the free arms.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

Hydrogel Formation

In general, precursors may be combined in a flowable composition with a delayed crosslinking chemistry to make a covalently-crosslinked material in situ that comprises a therapeutic agent that is released over a suitable period of time. The crosslinking reactions generally occur in aqueous solution under physiological conditions. The crosslinking reactions preferably do not release heat of polymerization or require exogenous energy sources for initiation or to trigger polymerization. Photochemical initiation, for instance, is generally to be avoided in the eye so as to avoid damage to the eye. In the case of injected materials, the viscosity may be controlled so that the material is introduced through a small diameter catheter or needle. In the case of materials applied around an eye, which are optionally delivered through such a catheter/needle, viscosity may further be controlled to keep precursors in place until they form a gel so that the precursors do not run-off the intended site of use.

The hydrogel is generally low-swelling, as measurable by the hydrogel having a weight increasing no more than about 0% to about 10% or to about 50% upon exposure to a physiological solution for twenty-four hours relative to a weight of the hydrogel at the time of formation. One embodiment for reducing swelling is to increase the number of crosslinks, bearing in mind, however, that crosslinks can increase rigidity or brittleness. Another embodiment is to reduce the average chain distance between crosslinks. Another embodiment is to use precursors with many arms, as explained below.

Another embodiment to reduce swelling is to control the degree of hydrophilicity, with less hydrophilic materials tending to swell less; for instance, highly hydrophilic materials such as PEOs can be combined with less hydrophilic materials such as PPO or even hydrophobic groups such as alkyls.

Another embodiment to reduce swelling is to choose precursors that have a high degree of solvation at the time of crosslinking but subsequently become less solvated and having a radius of solvation that effectively shrinks; in other words, the precursor is spread-out in solution when crosslinked but later contracts. Changes to pH, temperature, solids concentration, and solvent environment can cause such changes; moreover, an increase in the number of branches (with other factors being held effectively constant) will tend to also have this effect. The number of arms are believed to sterically hinder each other so that they spread-out before crosslinking, but these steric effects are offset by other factors after polymerization. In some embodiments, precursors have a plurality of similar charges so as to achieve these effects, e.g., a plurality of functional groups having a negative charge, or a plurality of arms each having a positive charge, or each arm having a functional group of similar charges before crosslinking or other reaction.

Hydrogels described herein can include hydrogels that swell minimally after deposition. Such medical low-swellable hydrogels may have a weight upon polymerization that increases no more than, e.g., about 50%, about 10%, about 5%, about 0% by weight upon exposure to a physiological solution, or that shrink (decrease in weight and volume), e.g., by at least about 5%, at least about 10%, or more. Artisans will immediately appreciate that all ranges and values within or otherwise relating to these explicitly articulated limits are disclosed herein. Unless otherwise indicated, swelling of a hydrogel relates to its change in volume (or weight) between the time of its formation when crosslinking is effectively complete and the time after being placed in vitro a physiological solution in an unconstrained state for twenty-four hours, at which point it may be reasonably assumed to have achieved its equilibrium swelling state. For most embodiments, crosslinking is effectively complete within no more than about fifteen minutes such that the initial weight can generally be noted at about 15 minutes after formation as Weight at initial formation. Accordingly, this formula is used: % swelling=[(Weight at 24 hours−Weight at initial formation)/Weight at initial formation]*100. n the case of hydrogels that have substantial degradation over twenty-four hours, the maximum weight may be used instead of a 24-hour weight, e.g., as measured by taking successive measurements. The weight of the hydrogel includes the weight of the solution in the hydrogel. A hydrogel formed in a location wherein it is constrained is not necessarily a low-swelling hydrogel. For instance, a swellable hydrogel created in a body may be constrained from swelling by its surroundings but nonetheless may be a highly swellable hydrogel as evidenced by measurements of its swelling when unconstrained and/or the forces against a constraint.

Reaction kinetics are generally controlled in light of the particular functional groups unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction, so that some embodiments have at least one precursor with a molecular weight of at least 5,000 to 50,000 or 150,000 Daltons. Preferably the crosslinking reaction leading to gelation occurs within about 2 to about 10 or to about 30 minutes; artisans will immediately appreciate that all the ranges and values within the explicitly stated ranges are contemplated, e.g., at least 120 seconds, or between 180 to 600 seconds. Gelation time is measured by applying the precursors to a flat surface and determining the time at which there is substantially no flow down the surface when it is titled at an angle of about 60 degrees (i.e., a steep angle, close to perpendicular).

The crosslinking density of the resultant biocompatible crosslinked polymer is controlled by the overall molecular weight of the crosslinker and functional polymer and the number of functional groups available per molecule. A lower molecular weight between crosslinks such as 500 will give much higher crosslinking density as compared to a higher molecular weight such as 10,000. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. Precursors with longer distances between crosslinks are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 3,000 to 100,000 or, e.g., 10,000 to 35,000.

The solids content of the hydrogel can affect its mechanical properties and biocompatibility and reflects a balance between competing requirements. In general, a relatively low solids content tends to be most useful, e.g., between about 2.5% to about 25%, including all ranges and values there between, e.g., about 2.5% to about 10%, about 5% to about 15%, or less than about 15%.

Anatomy of the Eye

The structure of the mammalian eye can be divided into three main layers or tunics: the fibrous tunic, the vascular tunic, and the nervous tunic. The fibrous tunic, also known as the tunica fibrosa oculi, is the outer layer of the eyeball consisting of the cornea and sclera. The sclera is the supporting wall of the eye and gives the eye most of its white color. It is extends from the cornea (the clear front section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. It helps lubricate the eye by producing mucus and tears, although a smaller volume of tears than the lacrimal gland. The conjunctiva is typically divided into three parts: (a) Palpebral or tarsal conjunctivam which is the conjunctiva lining the eyelids; the palpebral conjunctiva is reflected at the superior fornix and the inferior fornix to become the bulbar conjunctiva. (b) Fornix conjunctiva: the conjunctiva where the inner part of the eyelids and the eyeball meet. (c) Bulbar or ocular conjunctiva: The conjunctiva covering the eyeball, over the sclera. This region of the conjunctiva is bound tightly and moves with the eyeball movements.

The conjunctiva effectively surrounds, covers, and adheres to the sclera. It is has cellular and connective tissue, is somewhat elastic, and can be removed, teased away, or otherwise taken down to expose a surface area of the sclera. As explained below, it can be removed or used in conjunction with transcleral drug delivery schemes.

The vascular tunic, also known as the tunica vasculosa oculi, is the middle vascularized layer which includes the iris, ciliary body, and choroid. The choroid contains blood vessels that supply the retinal cells with oxygen and remove the waste products of respiration.

The nervous tunic, also known as the tunica nervosa oculi, is the inner sensory which includes the retina. The retina contains the photosensitive rod and cone cells and associated neurons. The retina is a relatively smooth (but curved) layer. It does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

The cornea and lens help to converge light rays to focus onto the retina. The lens, behind the iris, is a convex, springy disk which focuses light, through the second humour, onto the retina. It is attached to the ciliary body via a ring of suspensory ligaments known as the Zonule of Zinn. The ciliary muscle is relaxed to focus on an object far away, which stretches the fibers connecting it with the lens, thus flattening the lens. When the ciliary muscle contracts, the tension of the fibers decreases, which brings the lens back to a more convex and round shape. The iris, between the lens and the first humour, is a pigmented ring of fibrovascular tissue and muscle fibers. Light must first pass though the center of the iris, the pupil. The size of the pupil is actively adjusted by the circular and radial muscles to maintain a relatively constant level of light entering the eye.

Light enters the eye, passes through the cornea, and into the first of two humors, the aqueous humour. Approximately two-thirds of the total eyes refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it: the vitreous humor, retina, c, and optic nerve. On the other side of the lens is the second humour, the vitreous humour, which is bounded on all sides: by the lens, ciliary body, suspensory ligaments and by the retina. It lets light through without refraction, helps maintain the shape of the eye and suspends the delicate lens.

Figure 4:
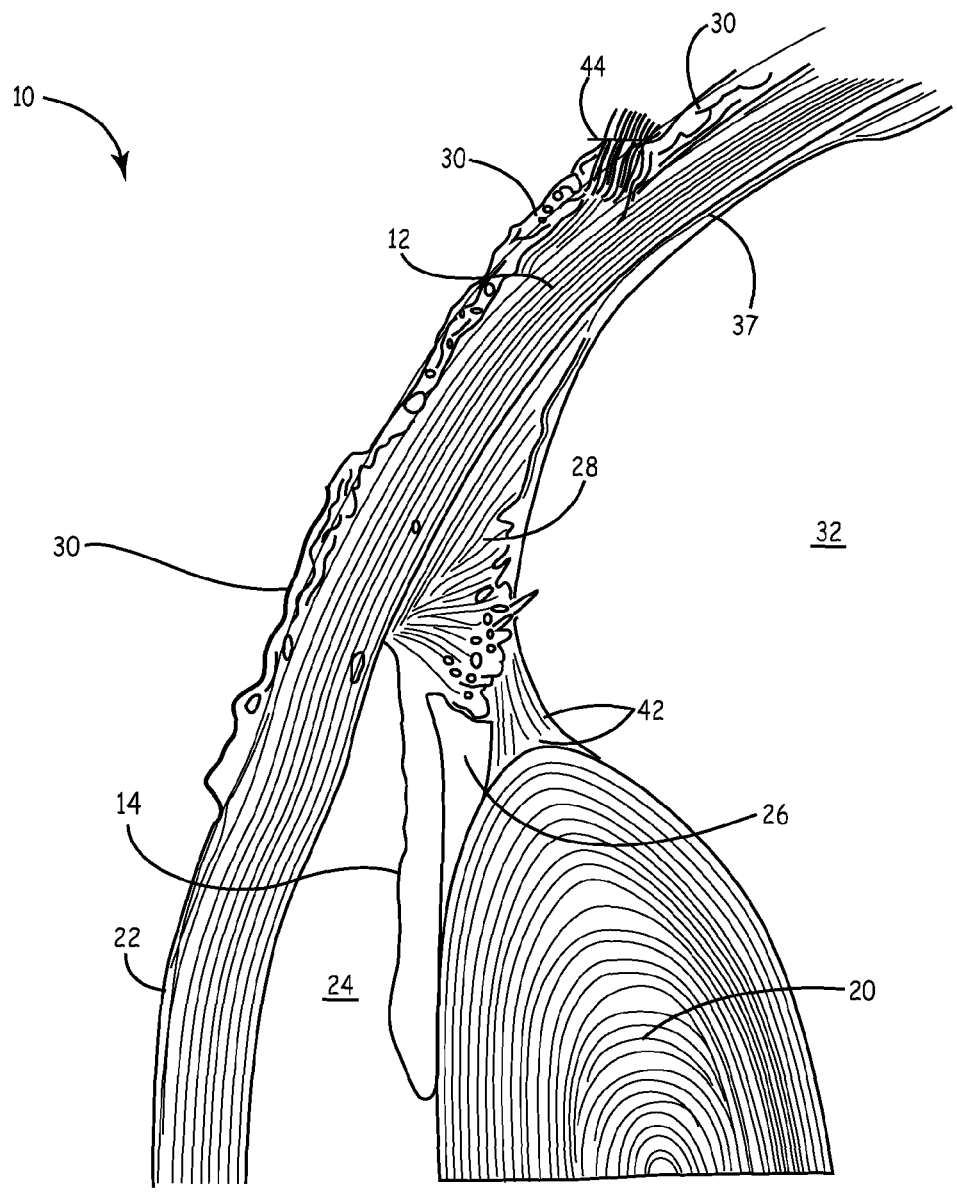
FIG. 4 is an enlarged view of the cross-sectional view of FIG. 3.

FIG. 1 depicts eye 10 having sclera 12, iris 14, pupil 16, and eyelid 18. FIG. 2 depicts a perspective view of eye 10 with a partial cross-section that depicts lens 20, inferior oblique muscle 22, inferior rectus muscle 24, and optic nerve 26. FIG. 3 is a cross-section of eye 10 and depicts cornea 22 that is optically clear and allows light to pass iris 14 and penetrate lens 20. Anterior chamber 24 underlies cornea 22 and posterior chamber 26 lies between iris 14 and lens 20. Ciliary body 28 is connected to lens 20. FIG. 3 depicts a portion of the conjunctiva 30, which overlies the sclera 12. The vitreous body 32 comprises the jelly-like vitreous humor, with hyaloid canal 34 being in the same. Fovea 36 is in the macula and retina 38 overlies choroid 37. Zonular spaces 42 are depicted. FIG. 4 shows eye 10 in partial view, and shows portions of conjunctiva 30 on sclera 12, including tendon of the superior rectus muscle 44 emerging from the same.

Figure 5:
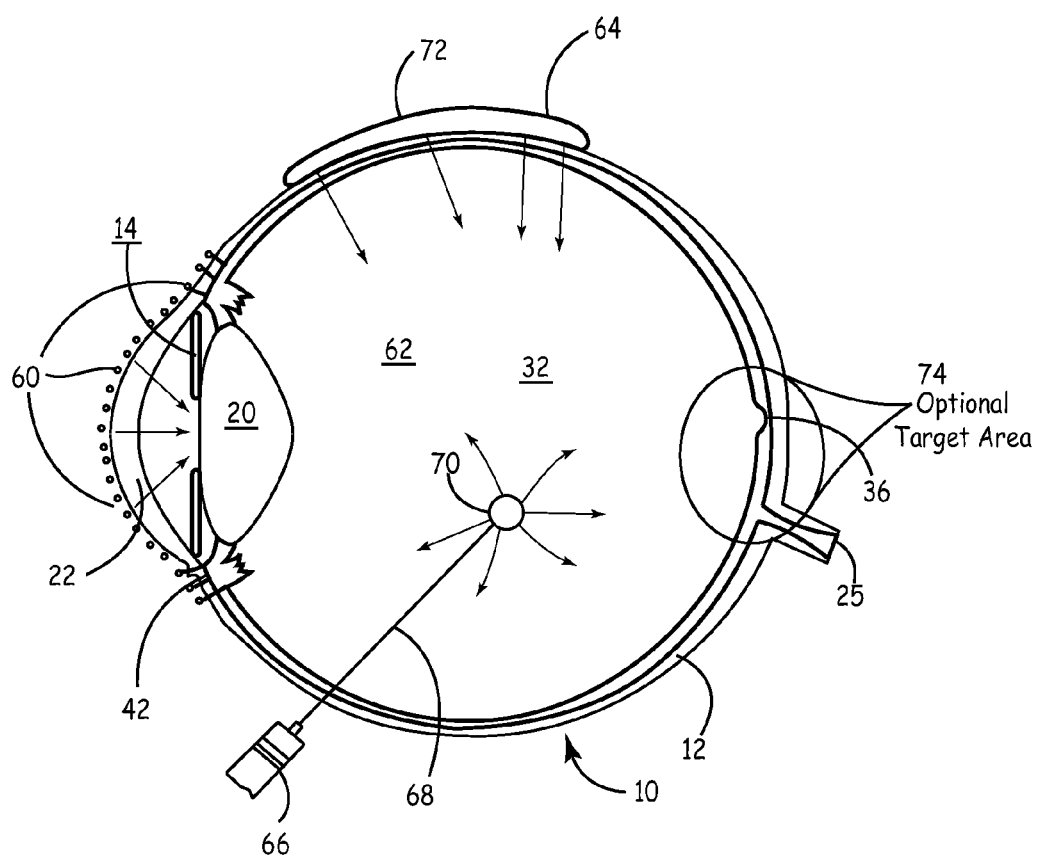
FIG. 5 depicts various delivery alternatives for the implants.

FIG. 5 shows certain points of delivery at or near eye 10. One area is topically at 60, with area 60 being indicated by dots on surface of eye 10. Another area is intravitreally as indicated by numeral 62, or trans-sclerally, as indicated by numeral 64. In use, for example a syringe 66, catheter (not shown) or other device is used to deliver hydrogel or a hydrogel precursors, optionally through needle 68, into the eye, either intravitrealy, as at 70 or peri-ocularly, as at 72. Drugs or other therapeutic agents are released to the intra-ocular space. In the case of back-of-the-eye diseases, drugs may be targeted via the peri-ocular or intravitreal route to target approximate area 74, where they interact with biological features to achieve a therapy.

Eye Disease States

The materials described herein may be used to deliver drugs or other therapeutic agents (e.g., imaging agents or markers) to eyes or tissues nearby. Some of the disease states are back-of-the-eye diseases. The term back-of-the eye disease is recognized by artisans in these fields of endeavor and generally refers to any ocular disease of the posterior segment that affects the vasculature and integrity of the retina, macula or choroid leading to visual acuity disturbances, loss of sight or blindness. Disease states of the posterior segment may result from age, trauma, surgical interventions, and hereditary factors. Some back-of-the-eye disease are; age-related macular degeneration (AMD) cystoid macular edema (CME), diabetic macular edema (DME), posterior uveitis, and diabetic retinopathy. Some back-of-the-eye diseases result from unwanted angiogenesis or vascular proliferation, such as macular degeneration or diabetic retinopathy. Drug treatment options for these and other conditions are further discussed elsewhere herein.

Application of Precursors to form Hydrogels In Situ

One mode of application is to apply a mixture of precursors and other materials (e.g., therapeutic agent, viscosifying agent, accelerator, initiator) through a needle, cannula, catheter, or hollow wire to a site in or near an eye. The mixture may be delivered, for instance, using a manually controlled syringe or mechanically controlled syringe, e.g., a syringe pump. Alternatively, a dual syringe or multiple-barreled syringe or multi-lumen system may be used to mix the precursors at or near the site.

One system that has been tested involved mixing a drug into a diluent, and drawing 200 microliters of the drug/diluent into a 1 ml syringe. About 66 mg of a precursor powder consisting of trilysine was placed into a separate 1 ml syringe. The two syringes were attached via a female-female LUER connector, the solution was moved back and forth between the syringes until the dry precursor was completely dissolved. A solution of multi-armed electrophilic precursor in 200 µl of water was drawn into a third 1-ml syringe. Using another female-female LUER connector, the user mixed the reconstituted PEG/drug solution with the electrophilic precursor. The solutions were rapidly inject back and forth at least about ten times to ensure good mixing. The solutions were drawn into 1 syringe and were then available for further use.

Sites where drug delivery depots may be formed include the anterior chamber, the vitreous, episcleral, in the posterior subtenon's space (Inferior fornix), subconjunctival, on the surface of the cornea or the conjunctiva, among others.

Back of the eye diseases can be treated with drugs utilizing, e.g., topical, systemic, intraocular and subconjunctival delivery routes. Systemic and topical drug delivery modalities fall short in delivering therapeutic drug levels to treat posterior segment diseases. These methods of drug delivery encounter diffusion and drug dilution issues due to the inherent anatomical barriers of the intraocular and systemic systems, causing significant patient side effects (due to multiple daily dosing), poor bioavailability and compliance issues. Pericular drug delivery of an ophthalmic hydrogel implant using subconjunctival, retrobulbar or sub-Tenon's placement has the potential to offer a safer and enhanced drug delivery system to the retina compared to topical and systemic routes.

The delivery site for placement of an intraocular drug delivery implant is generally dependent upon the disease that needs to be treated and the type of drug therapy. For example; steroids like dexamethasone and triamicinolone acetonide may be mixed with the hydrogel precursor to form a sustained-release drug implant. The liquid hydrogel could then be injected in-situ into the sub-Tenon's capsule where it could deliver a constant or tunable release profile of the drug over and over a three to four month time period. The minimally invasive procedure could be performed in a doctor's office, or after a cataract operation under topical anesthesia, to treat chronic back of the eye diseases.

Figure 6A:
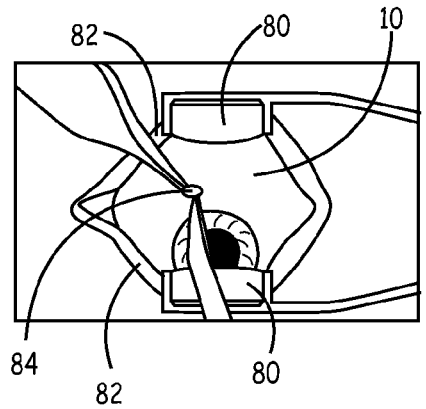
FIG. 6A depicts introduction of an implant into the eye, with a small opening being made
Figure 6B:
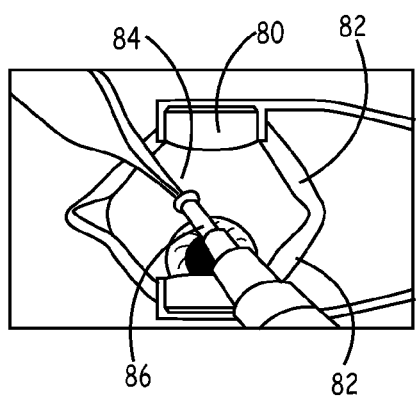
FIG. 6B depicts the method of FIG. 6A, with a cannula introduced through the opening.
Figure 6C:
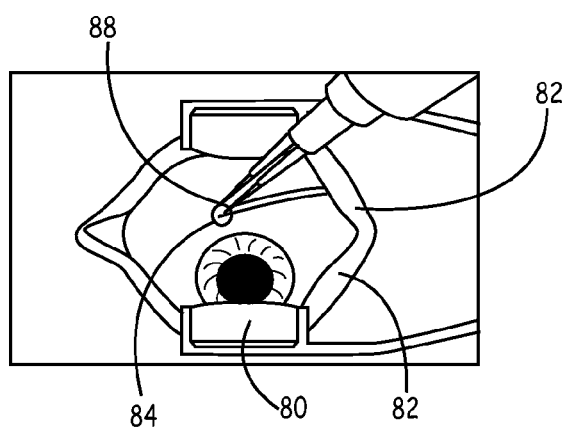
FIG. 6C depicts the method of FIG. 6B, with closure of the opening by cauterization

In some embodiments, a retractor 80 is used to hold back eyelids 82, and the user would create a small buttonhole 84 (FIG. 6A) in the conjunctiva about 5-6 mm from the inferior/nasal limbus and dissect the conjunctiva down through Tenon's capsule; to the bare sclera. Next, a 23-gauge blunt cannula 86 (e.g., 15 mm in length) is inserted through the opening and the liquid drug implant is injected onto the scleral surface (FIG. 6B). The cannula is then removed and the conjunctive is closed with a cauterization device 88 (FIG. 6C).

One advantage of an implant having three dimensional integrity is that it will tend to resist cellular infiltration and be able to prevent the locally administered drug from being phagocytosed and cleared prematurely from the site. Instead, it stays in place until delivered. By way of contrast a microparticle, liposome, or pegylated protein tends to be rapidly cleared from the body by the reticuloendothelial system before being bioeffective.

Intravitreal Drug Delivery Implants

The delivery of therapeutic amounts of a drug to the retina in posterior segment eye diseases remains a challenge. Although intravitreal injections into the vitreous cavity of anti-VEGF agents have shown promise to arrest and in some cases reverse chronic age-related diseases like macular degeneration, these techniques and procedures are not without risks and side effects. Intravitreal administration of therapeutic agents into the vitreous cavity can cause cataracts, endophthalmitis and retinal detachments. This form of therapy requires many patients to receive monthly intraocular injections of an anti-VEGF drug over a 12 month time period thus increasing the risk of infection, vitreous wicks and retinal detachments. Embodiments directed to an in situ hydrogel biodegradable drug implant will provide an effective alternative treatment for back of the eye diseases, and are expected to reduce the common side-effects associated with repeated intravitreal injections. Embodiments of an intravitreal biodegradable drug delivery implant system are summarized below.

Figure 7A:
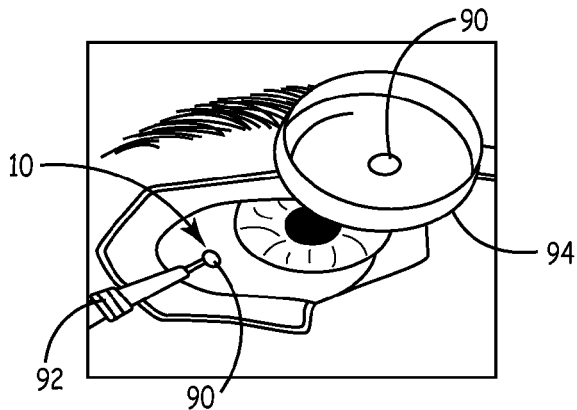
FIG. 7A depicts delivery of implants in the intravitreal space, with an opening being made on the eyes surface.
Figure 7B:
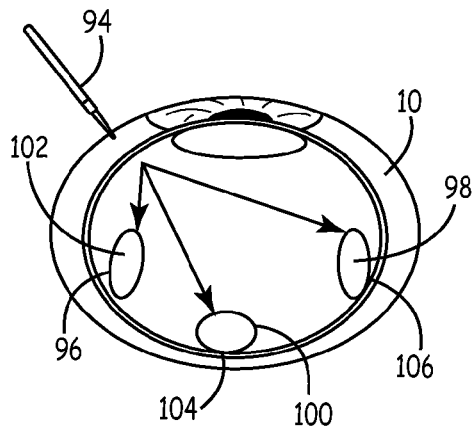
FIG. 7B depicts the method of FIG. 7A with a cannula for delivery of an implant to one or more locations internal to the eye.

In FIG. 7A, a hydrogel implant is injected intravitrealy about 2.5 mm posterior to the limbus through a pars plana incision 90 using a sub-retinal cannula 92, as shown by depiction of magnifying glass 94 held so as to visualization incision 90 on eye 10, which may be made following dissecting-away or otherwise clearing the conjunctiva, as needed. A 25, 27 or 30 gauge sub-retinal cannula 94 (or other appropriate cannulas) is then inserted through incision 90 and positioned intraocularly to the desired target site, e.g., at least one of sites 96, 98, 100 (FIG. 7B) where the flowable precursors are introduced to form a hydrogel in-situ. The precursors then forms into an absorbable gel 102, 104, and/or 106, adhering to the desired target site.

As described in more detail in other sections, a drug depot of the in-situ hydrogel drug delivery implant may be designed for controlled, long term drug release ranging from, e.g., about one to about three months; and may optionally be directed to treatment of diseases of the posterior segment including, for example, age-related macular degeneration, diabetic retinopathy, diabetic macular edema, and the cystoid macular. The device can carry a drug payload of various types of therapeutic agents for various conditions, of which some include, for example, steroids, antibiotics, NSAIDS and/or antiangiogenic agents, or combinations thereof.

Figure 8:
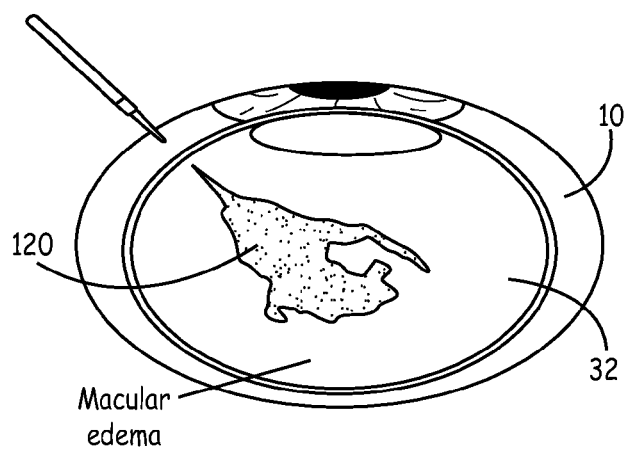
FIG. 8 depicts delivery of a bolus of a material into an eye.

The in-situ implant embodiments can improve the efficacy and pharmacokinetics of potent therapeutic agents in the treatment of chronic back of the eye diseases and minimize patient side effects in several ways. First, the implant can be placed in the vitreous cavity at a specific disease site, bypassing the topical or systemic routes and thereby increasing drug bioavailability. Secondly, the implant maintains local therapeutic concentrations at the specific target tissue site over an extended period of time. Thirdly, the number of intravitreal injections would be substantially reduced over a 12 month therapy regimen, thereby reducing patient risk of infection, retinal detachment and transient visual acuity disturbances (white specks floating in the vitreous) that can occur until the drug in the vitreous migrates down toward the inferior wall of the eye and away from the portion of the central vitreous or macula. As shown in FIG. 8, a bolus 120 of conventionally-injected drugs forms in the vitreous body and displaces the vitreous humor until dispersed. Dispersion typically takes a significant amount of time since the vitreous humor is quite viscous. The bolus thus interferes with vision, particularly when it is moved around the eye in response to sudden accelerations, e.g., as the patient stands up or quickly turns the head.

Trans-Scleral Drug Delivery

The hydrogels may be formed on scleral tissue either with or without the presence of the conjunctiva. The hydrogel may be adhesive to the sclera or other tissue near the sclera to promote drug diffusion through the intended tissue or to provide a stable depot to direct the therapeutic agents as required. In some embodiments, the conjunctiva of the eye may be removed, macerated, dissected away, or teased-free so that the tissue can be lifted away from the sclera to access a specific region of the sclera for implantation or injection of the hydrogel. A hydrogel is formed in situ that makes a layer on, and adheres, to the surface area. The conjunctiva may be allowed to contact the tissue if it is still present or retains adequate mechanical integrity to do so. In some embodiments the hydrogel is comprised of at least 50%, 75%, 80%, 90%, or 99% w/w water-soluble precursors (calculated by measuring the weight of the hydrophilic precursors and dividing by the weight of all precursors, so that the weight of water or solvents or non-hydrogel components is ignored) to enhance the non-adhesive properties of the hydrogel. In some embodiments, such hydrophilic precursors substantially comprise PEOs. In some embodiments, drugs to reduce tissue adherence mediated by biological mechanisms including cell mitosis, cell migration, or macrophage migration or activation, are included, e.g., anti-inflammatories, anti-mitotics, antibiotics, PACLITAXEL, MITOMYCIN, or taxols.

In other embodiments, the sclera is not substantially cleared of the conjunctiva. The conjunctiva is a significant tissue mass that overlays much or all of the sclera. The conjunctiva may be punctured or penetrated with a needle or catheter or trocar and precursors introduced into a space between the sclera and conjunctiva. In some cases the conjunctiva may be punctured to access a natural potential space between the tissues that is filled by the precursors. In other cases, a potential or actual space is created mechanically with a trocar, spreader, or the like, that breaks the adherence between the sclera and conjunctiva so that precursors may be introduced. The conjunctiva has enough elasticity to allow useful amounts of precursors to be introduced or forced into such natural or created spaces. Similarly, in the case of intravitreal hydrogel formation, relatively large columns may also be used. Accordingly, in some cases, the amount is between about 0.25 to about 10 ml; artisans will immediately appreciate that all the ranges and values within the explicitly stated ranges are contemplated, e.g., about 1 ml or from 0.5 ml to about 1.5 ml.

Moreover, removal of a hydrogel, whether present intraocularly or periocularly, is also readily achieved using either a vitrectomy cutter if the implant is located in the vitreous cavity or a manual I/A syringe and cannula if the implant is located on the scleral surface or irrigation/aspiration handpiece. This contrasts with major surgical procedures needed for the removal of some conventional non-absorbable implants.

In some aspects, in-situ formation of the hydrogel lets the hydrogel gel or crosslink in place, so that it does not flow back out through the tract of the needle and diffuse extraocularly through the incision site upon the removal of the needle or cannula. A shape-stable hydrogel thus formed can effectively deliver the drug and advantageously can have well-controlled size, shape, and surface area. A small needle may be used to inject the materials since soluble or flowable precursors may be used instead of an already-formed material. By way of contrast, alternative materials that do not cross-link quickly and firmly upon introduction tend to flow back out of the incision. And materials that do not covalently cross-link are subject to creep or weeping as the material continually reorganizes and some or all of the material flows out.

Delivery across the sclera is an important advance in these arts that is made possible by the hydrogels and other materials disclosed herein. Transcleral drug delivery would conventionally not be considered since the diffusion of the drug across the scleral tissue is an unknown. Not only is the actual diffusion of the drug an issue, but the rate of that potential diffusion had to be balanced against the competing tendency of the drug to diffuse away to other relatively more permeable tissues, especially in response to tear or other fluid production. Moreover, fluid production in response to irritation is also a potential factor, e.g., as by flow of tears, lymph, edema, or a foreign body response. But the biocompatible materials and various available features, e.g., softness, biocompatible degradation products, conformability to surrounding tissues, adherence to the sclera, applicability over, in, or under the conjunctiva, crosslinking, non-irritating shape and deposition techniques, can be used to make suitable materials.

Adherence

Adhesivity can play an important role for in situ hydrogel-based therapies. For instance, a hydrogel that is adhesive to a scleral tissue can have good surface-area contact with the sclera to promote diffusion of drugs or other agents into the sclera. By way of contrast, a failure to adhere will create a diffusion barrier or allow entry of fluids between the drug depot and eye so that the drugs are washed away. On the other hand, if a peri-ocular hydrogel adheres to the tissues around it, or allows tissues to grow and adhere to it, the delivery of the drug may be compromised. Thus a hydrogel depot that adheres tenaciously to the sclera (the hydrogel's anterior surface) but does not adhere to tissues on its opposing surface (the posterior surface for a coating) or surfaces (for more complex geometries) would be useful. The in-situ made materials can reconcile these opposing needs by allowing forming the material in situ on the sclera with its other surfaces being free or substantially free of tissue contact during the time of gelation and/or crosslinking. As already explained, some embodiments relate to providing hydrogels that adhere to specific sites, e.g., the sclera and/or conjunctiva.

A test of adherence of a hydrogel to a tissue is, unless otherwise indicated, to apply it to a rabbit cornea and show that it is immobilized and is not displaced when placed on an uninjured rabbit cornea, despite unrestricted blinking by the rabbit. By way of contrast, a non-adherent material will be pushed out of, or to the side of the eye.

Some embodiments of forming a hydrogel involve mixing precursors that substantially crosslink after application to a surface, e.g., on a tissue of a patient to form a biodegradable hydrogel depot. Without limiting the invention to a particular theory of operation, it is believed that reactive precursor species that crosslink after contacting a tissue surface will form a three dimensional structure that is mechanically interlocked with the coated tissue. This interlocking contributes to adherence, intimate contact, and essentially continuous coverage of the coated region of the tissue. Moreover, formulations with strongly electrophilic functional groups may tend to react with nucleophilic groups on the tissue to form covalent crosslinks, provided that the electrophiles are present in suitable concentrations and the nucleophiles are at a suitable pH.

By way of contrast, conventional materials tend to be non-adhesive to an ocular surface. Lenticels made of hydrogels, for instance, are not adherent. Fibrin glue, for instance, is generally not adherent as that term is used herein, although the fact that it may stick somewhat to an ocular tissue is acknowledged. Moreover, for many materials, it is generally unknown whether or not they will be adherent to an ocular tissue, or to a particular ocular tissue.

Another aspect of adherence is that the implant is prevented from moving from the site of its intended use. This tends to increase patient comfort, reduce irritation, and reduce tearing or fluid-flowing reactions that affect the therapeutic agent in the implant. Also, the implant may be placed with precision, e.g., between certain tissues or on a tissue, with confidence that it will continue to affect the intended site.

Adherence can be useful for drug delivery. In some embodiments, specific zones are targeted for adherence, e.g., as in FIG. 5. For instance a material with the drug can be made to adhere to the sclera and/or conjunctiva. Or the material can be made to adhere to a surface inside the eye, a surface in the anterior portion of the eye. In some cases, the material is targeted to adhere to a surface inside the eye and within 1-10 mm of the macula; artisans will immediately appreciate that all the ranges and values within the explicitly stated ranges are contemplated, e.g., less than 10, 9, 8, 7, 6, 5, 4 mm or at least 1-10 mm or 2 mm up to about 25 mm distant; such targeting may be performed to avoid the macula itself, or not, as needed. Alternatively or example, such targeting may be used to place the material is a position to an interior side of the eye where it does not intrude into the light path through the eye to the retina.

Drugs or other Therapeutic Agents for Delivery

The hydrogel may be used to deliver classes of drugs including steroids, Non-steroidal anti-inflammatory drugs (NSAIDS), intraocular pressure lowering drugs, antibiotics, or others. The hydrogel may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The rate of release from the hydrogel will depend on the properties of the drug and the hydrogel, with factors including drug sizes, relative hydrophobicities, hydrogel density, hydrogel solids content, and the presence of other drug delivery motifs, e.g., microparticles.

The hydrogel precursor may be used to deliver classes of drugs including steroids, NSAIDS (See Table 1), intraocular pressure lowering drugs, antibiotics, pain relievers, inhibitors or vascular endothelial growth factor (VEGF), chemotherapeutics, anti-viral drugs etc. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations. The drugs that have low water solubility may be incorporated, e.g., as particulates or as a suspension. Higher water solubility drugs may be loaded within microparticles or liposomes. Microparticles can be formed from, e.g., PLGA or fatty acids.

TABLE 1

NSAIDS that may be delivered.

| Item | Drug | Structure | Solubility |
|---|---|---|---|
| 1 | Ibuprofen | 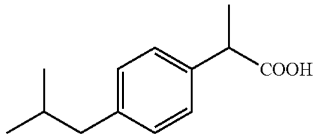 | 10 mg/ml @ pH 7 |
| 2 | Meclofenamate Sodium | 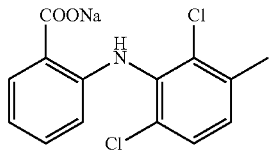 | <50 µg/mL @ pH 7.2<br>50 mg/mL @ pH 9.0 |
| 3 | Mefanamic Acid | 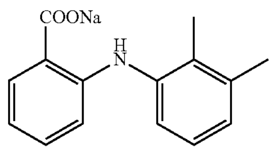 | 40 µg/ml @ pH 7.1 |
| 4 | Salsalate | 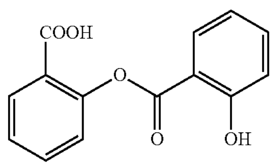 [SMILES: O=C(Oc1ccccc1C(=O)O)c1ccccc1O] | |
| 5 | Sulindac | 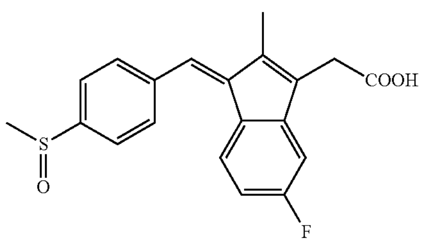 [SMILES: CC1=C(CC(=O)O)c2cc(F)ccc2/C1=C\c1ccc(S(C)=O)cc1] | Practically insoluble below pH 4.5: Very soluble >pH 6 |
| 6 | Tolmetin Sodium | 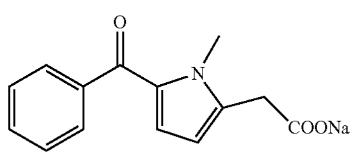 | Freely soluble in water |
| 7 | Ketoprofen | 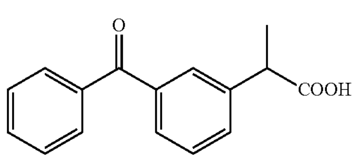 [SMILES: CC(C(=O)O)c1cccc(C(=O)c2ccccc2)c1] | Not less than 0.25 mg/ml @ pH 7.35 |
| 8 | Diflunisal | 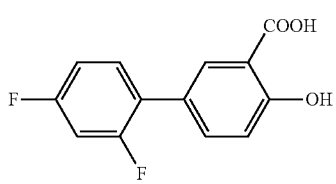 [SMILES: O=C(O)c1cc(-c2ccc(F)cc2F)ccc1O] | 3.43 mg/ml @ pH 7 |

TABLE 1-continued

NSAIDS that may be delivered.

| Item | Drug | Structure | Solubility |
|---|---|---|---|
| 9 | Piroxicam | 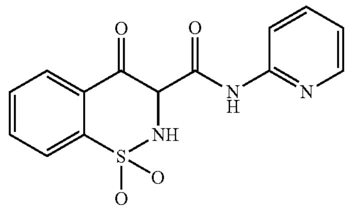 [SMILES: O=C(Nc1ccccn1)C1NS(O)(O)c2ccccc2C1=O] | 0.03 mg/ml |
| 10 | Naproxen | 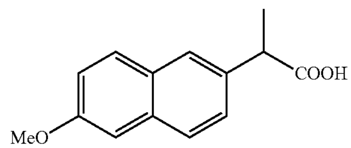 [SMILES: COc1ccc2cc(C(C)C(=O)O)ccc2c1] | Freely soluble at pH 8 |
| 11 | Etodolac | 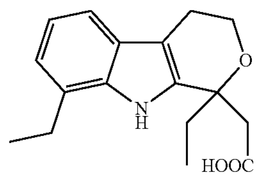 [SMILES: CCc1cccc2c3c([nH]c12)C(CC)(CC(=O)O)OCC3] | Insoluble in water |
| 12 | Flurbiprofen | 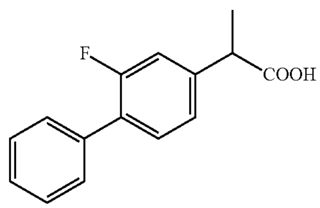 [SMILES: CC(C(=O)O)c1ccc(-c2ccccc2)c(F)c1] | 0.9 mg/mL |
| 13 | Fenoprofen Calcium | 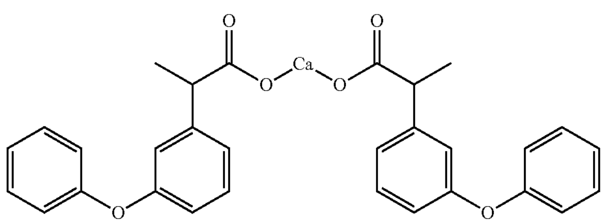 | Slightly soluble in water |
| 14 | Indomethacin | 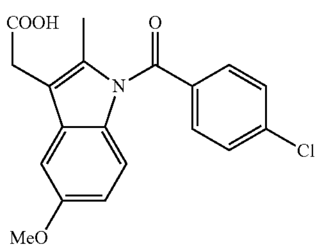 [SMILES: COc1ccc2c(c1)c(CC(=O)O)c(C)n2C(=O)c1ccc(Cl)cc1] | @ pH 7<br>Form I: 0.54 mg/ml<br>Form II: 0.80 mg/ml |
| 15 | Celecoxib | 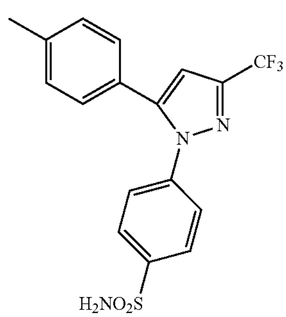 [SMILES: Cc1ccc(-c2cc(C(F)(F)F)nn2-c2ccc(S(N)(=O)=O)cc2)cc1] | 5 μg/ml |

TABLE 1-continued

NSAIDS that may be delivered.

| Item | Drug | Structure | Solubility |
| --- | --- | --- | --- |
| 16 | Ketorolac | 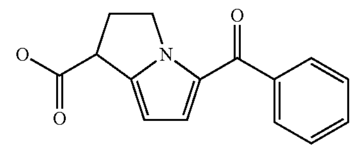 [SMILES: O=C(c1ccccc1)c1ccc2n1CCC2C(=O)O] | 10.5 mg/ml in IPB; 25 mg/ml as tromethamine salt. |
| 17 | Nepafenac | 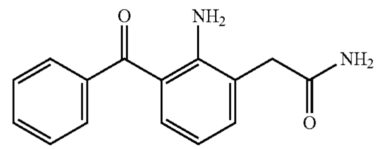 [SMILES: NC(=O)Cc1cccc(C(=O)c2ccccc2)c1N] | <1 mg/ml (The drug is available as 0.1% suspension) |

In some embodiments, the therapeutic agent is mixed with the precursors prior to making the aqueous solution or during the aseptic manufacturing of the functional polymer. This mixture then is mixed with the precursor to produce a crosslinked material in which the biologically active substance is entrapped. Functional polymers made from inert polymers like PLURONIC, TETRONICS or TWEEN surfactants are preferred in releasing small molecule hydrophobic drugs.

In some embodiments, the therapeutic agent or agents are present in a separate phase when crosslinker and crosslinkable polymers are reacted to produce a crosslinked polymer network or gel. This phase separation prevents participation of bioactive substance in the chemical crosslinking reaction such as reaction between NHS ester and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(g-lycolic acid), poly(lactic acid), poly(glycolic acid)-co-poly (glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone) s and poly (hydroxy acid) are particularly preferred as biodegradable encapsulation vehicles.

In using crosslinked materials which are described herein as drug delivery vehicles, the active agent or encapsulated active agent may be present in solution or suspended form in crosslinker component or functional polymer solution component. The nucleophilic component, whether it be in the crosslinker or the functional polymer is the preferred vehicle due to absence of reactive groups. The functional polymer along with bioactive agent, with or without encapsulating vehicle, is administered to the host along with equivalent amount of crosslinker and aqueous buffers. The chemical reaction between crosslinker and the functional polymer solution readily takes place to form a crosslinked gel and acts as a depot for release of the active agent to the host. Such methods of drug delivery find use in both systemic and local administration of an active agent.

A variety of drugs or other therapeutic agents may be delivered using these systems. A list of agents or families of drugs and examples of indications for the agents are provided. The agents may also be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefrin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma.

In using the crosslinked composition for drug delivery as mentioned above, the amount of crosslinkable polymer, crosslinker and the dosage agent introduced in the host will necessarily depend upon the particular drug and the condition to be treated. Administration may be by any convenient means such as syringe, cannula, trocar, catheter and the like.

Certain embodiments of the invention are accomplished by providing compositions and methods to control the release of relatively low molecular weight therapeutic species using hydrogels. A therapeutic agent first is dispersed or dissolved within one or more relatively hydrophobic rate modifying agents to form a mixture. The mixture may be formed into particles or microparticles, which are then entrapped within a bioabsorbable hydrogel matrix so as to release the water soluble therapeutic agents in a controlled fashion. Alternatively, the microparticles may be formed in situ during crosslinking of the hydrogel.

In one method, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments of the invention include compositions and methods for forming composite hydrogel-based matrices and microspheres having entrapped therapeutic compounds. In one embodiment, a bioactive agent is entrapped in microparticles having a hydrophobic nature (also termed hydrophobic microdomains), to retard leakage of the entrapped agent. In some cases, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with the present invention, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in commonly assigned U.S. Pat. Nos. 6,632,457; 6,379,373; and 6,514,534, each of which are hereby incorporated by reference. Moreover, drug delivery schemes as described in commonly owned Compositions And Methods For Controlled Drug Delivery From Biodegradable Hydrogels, now 60/899,898 filed Feb. 6, 2007, which is hereby incorporated by reference herein, may also be used with the hydrogels herein.

Controlled rates of drug delivery also may be obtained with the system disclosed herein by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

Biodegradation

The hydrogel is, in general, water-degradable, as measurable by the hydrogel being dissolvable in vitro in an excess of water by degradation of water-degradable groups. This test is predictive of hydrolytically-driven dissolution in vivo, a process that is in contrast to cell or protease-driven degradation. The hydrogels can be selected to be absorbable over days, weeks, or months, depending on the drug selected, disease being treated, the duration for release that is needed, and the release profile of the specific drug selected. Some embodiments, however, are specifically directed to 30 to 120 days since longer periods of time allow for less user-control of the dosing regimen, a factor that may be important if the drug does not exert its intended effect.

The biodegradable linkage may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Significantly, however, polyanhydrides or other conventionally-used degradable materials that degrade to acidic components tend to cause inflammation in the eye. The hydrogels, however, may exclude such materials, and may be free of polyanhydrides, anhydride bonds, or precursors that degrade into acid or diacids. Instead, for example, SG (succinimidyl glutarate), SS (succinimidyl succinate), SC (succinimidyl carbonate), carboxymethyl hydroxybutyric acid (CM-HBA) may be used and have esteric linkages that are hydrolytically labile.

If it is desired that the biocompatible crosslinked polymer be biodegradable or absorbable, one or more precursors having biodegradable linkages present in between the functional groups may be used. The biodegradable linkage optionally also may serve as the water soluble core of one or more of the precursors. For each approach, biodegradable linkages may be chosen such that the resulting biodegradable biocompatible crosslinked polymer will degrade or be absorbed in a desired period of time.

The crosslinked hydrogel degradation will generally proceed by the water-driven hydrolysis of the biodegradable segment when water-degradable materials are used. If polyglycolate is used as the biodegradable segment, for instance, the crosslinked polymer could be made to degrade in about 1 to about 30 days depending on the crosslinking density of the network. Similarly, a polycaprolactone based crosslinked network can be made to tend to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

Visualization Agents

A visualization agent may be used with the hydrogel; it reflects or emits light at a wavelength detectable to a human eye so that a user applying the hydrogel can observe the gel.

Preferred biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. These concentration ranges can give a color to the hydrogel without interfering with crosslinking times (as measured by the time for the reactive precursor species to gel).

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. The visualization agent may be present with either reactive precursor species, e.g., a crosslinker or functional polymer solution. The preferred colored substance may or may not become chemically bound to the hydrogel. The visualization agent may generally be used in small quantities, preferably less than 1% weight/volume, more preferably less that 0.01% weight/volume and most preferably less than 0.001% weight/volume concentration.

Additional machine-aided imaging agents may be used, such as fluorescent compounds, x-ray contrast agents (e.g., iodinated compounds) for imaging under x-ray imaging equipment, ultrasonic contrast agents, or MRI contrast agents (e.g., Gadolinium containing compounds).

Viscosity

A composition with the precursors mixed therein can be made with viscosity suitable for introduction through a small gauge needle using manual force. A small gauge needle has a diameter less than the diameter of a needle with a gauge of 27, e.g., 28, 29, 30, 31, 32, or 33 gauge, with the gauge being specific for inner and/or outer diameters. Moreover, hollow-tube wires, as used in the intravascular arts, may be used to deliver the materials, including those with inn and/or outer diameters equivalent to the small gauge needles, or smaller. Thus a viscosity of between about 1 to about 100,000 centipoise may be used; artisans will immediately appreciate that all the ranges and values within the explicitly stated ranges are contemplated e.g., about 10 to about 10,000 centipoise, less than about 5 to about 10,000 centipoise, less than about 100 or about 500 centipoise, or between about 1 and about 100 centipoise. The viscosity may be controlled, e.g., by choosing appropriate precursors, adjusting solids concentrations, and reaction kinetics. In general, lower concentrations of precursors, increased hydrophilicity, lower molecular weights favor a lower viscosity.

Viscosity enhancers may be used in conjunction with precursors. In general, the viscosity enhancers do not react with the precursors to form covalent bonds. While it is appreciated that precursors that are generally free of such bonding may sometimes participate in unwanted side reactions, these have little effect on the hydrogel so that the precursors are "free" of such reactions. For instance, if the precursors react by electrophile-nucleophile reactions, the viscosity enhancers may be free of electrophiles or nucleophiles that can form covalent bonds with functional groups of the precursors, even if there is some low level of unwanted side reactions. Viscosity enhancers are, in general, hydrophilic polymers with a molecular weight of at least 20,000, or from about 10,000 to about 500,000 Daltons; artisans will immediately appreciate that all values and ranges between these explicitly stated values are described, e.g., at least about 100,000 or 200,000. A concentration of about 5% to about 25% w/w may be used, for instance. PEG (e.g., M.W. 100,000 to 250,000) is useful, for example. Viscosity enhancers may be free of electrophiles and/or nucleophiles. Viscosity enhancers may be fee of one or more functional groups such as hydroxyl, carboxyl, amine, or thiol. Viscosity enhancers may include one or more biodegradable links as described herein for precursors. Viscosity enhancers can be useful to prevent precursors from running-off a tissue site before the precursor's crosslink to form a gel.

Overview

Certain polymerizable hydrogels made using synthetic precursors are known in the medical arts, e.g., as used in products such as FOCALSEAL (Genzyme, Inc.), COSEAL (Angiotech Pharmaceuticals), and DURASEAL (Confluent Surgical, Inc), as in, for example, U.S. Pat. Nos. 6,656,200; 5,874,500; 5,543,441; 5,514,379; 5,410,016; 5,162,430; 5,324,775; 5,752,974; and 5,550,187; each of which are hereby incorporated by reference to the extent they do not contradict what is explicitly disclosed herein. None of these materials seem to be suited to use inside the eye or around the eye. One reason is that they polymerize too quickly to be injected in a controlled fashion. Also, COSEAL and DURASEAL have a very high pH, which can be detrimental to ocular tissues (above pH 9). Another reason is that they apparently swell too much. The swelling of COSEAL and DURASEAL has been measured using an in vitro model in comparison to fibrin sealant (Campbell et al., Evaluation of Absorbable Surgical Sealants: In vitro Testing, 2005). Over a three day test, COSEAL swelled an average of about 558% by weight, DURASEAL increased an average of about 98% by weight, and fibrin sealant swelled about 3%. Assuming uniform expansion along all axes, the percent increase in a single axis was calculated to be 87%, 26%, and 1% for COSEAL, DURASEAL, and fibrin sealant respectively. FOCALSEAL is known to swell over 300%. And also needs an external light to be activated, so is not well suited as an injectable drug delivery depot, especially in or around the eye, which is sensitive to such radiation. Fibrin sealant is a proteinaceous glue that has adhesive, sealing, and mechanical properties that are inferior to COSEAL, DURASEAL, and other hydrogels disclosed herein. Further, it is typically derived from biological sources that are potentially contaminated, is cleared from the body by mechanisms distinct from water-degradation, and typically requires refrigeration while stored.

Some gel systems exist that relate to healing a wound or providing a lens on the cornea, e.g., as in U.S. Pat. Nos. 5,874,500, 6,458,889, 6,624,245 or PCT WO2006/031358 or WO2006/096586; other gels or systems for drug delivery are set forth in U.S. Pat. Nos. 6,777,000, 7,060,297, US2006/0182771, US2006/0258698, US2006/0100288, or US2006/0002963; each of which are hereby incorporated by reference to the extent they do not contradict what is explicitly disclosed herein.

Some systems to deliver drugs to the eye rely on topical eye drops. For example, after cataract and vitreoretinal surgery, antibiotics may need to be administered every few hours for several days. In addition, other drugs such as non-steroidal anti-inflammatory drugs (NSAIDS) may also need to be given frequently. Often some of these eye drops, for example RESTASIS (Allergan) also has a stinging and burning sensation associated with its administration. RESTASIS is indicated for dry eye and has to be used by the patient several times a day. Similarly treatments for other ophthalmic diseases such as cystoid macular edema, diabetic macular edema (DME), and diabetic retinopathy also need administration of steroidal or NSAID drugs. Several vascular proliferative diseases such as macular degeneration are treated using intravitreal injections of VEGF inhibitors. These include drugs such as LUCENTIS and AVASTIN (Genentech) and MACUGEN (OSI). Such drugs may be delivered using the hydrogel systems herein, with the steps of repeated dosings being avoided; e.g., not making new applications of the drug daily, weekly, or monthly, or not using topical eye drops to administer the drug.

Several alternative drug delivery systems are known. These other systems generally include intravitreal implant reservoir type systems, biodegradable depot systems, or implants that need to be removed (non-erodeable). The state of the art in this regard has been delineated in texts such as "Intraocular Drug Delivery" (Jaffe et al., Taylor & Francis pub., 2006. However, most of these implants either need to be removed at term, can detach from their target site, may cause visual disturbances in the back of the eye or can be inflammatory themselves because of the liberation of a substantial amount of acidic degradation products. These implants are thus made to be very small with a very high drug concentration. Even though they are small, they still need to be deployed with needles over 25G (25 gauge) in size, or a surgical approach delivery system for implantation or removal as needed. In general, these are localized injections of drug solutions into the vitreous humor or intravitreal implants that use a biodegradable-approach or a removable-reservoir approach.

For instance, localized injections delivered into the vitreous humor include anti-VEGF agents LUCENTIS or AVASTIN. POSURDEX (Allergan) is a biodegradable implant with indications for use being diabetic macular edema (DME) or retinal vein occlusions, with a 22 g delivery system used for delivery into the vitreous cavity; these are powerful drugs in a short drug delivery duration setting. The therapeutic agent is in dexamethasone with polylactic/polyglycolic polymer matrix. Phase III trials with POSURDEX for diabetic retinopathy are in progress.

And for instance, a Medidure implant (PSIVIDA) is used for DME indications. This implant is about 3 mm in diameter, cylindrical in shape, and non-erodeable. It is placed with a 25 gauge injector delivery system, the therapeutic agent is fluocinolone acetonide, and has a nominal delivery life of 18 months or 36 months (two versions). Phase III trials in progress.

Surmodics has a product that is an intravitreal, removable implant. It is placed surgically, with a therapeutic agent being triamcinolone acetonide. Its nominal delivery life is about two years. Its indication is for DME. It is presently in about Phase I trials.

In contrast to these conventional systems, hydrogels can be made that are biocompatible for the eye, which is an environment that is distinctly different from other environments. The use of minimally inflammatory materials avoids angiogenesis, which is harmful in the eye in many situations. Biocompatible ocular materials thus avoid unintended angiogenesis; in some aspects, avoiding acidic degradation products achieves this goal. Further, by using hydrogels and hydrophilic materials (components having a solubility in water of at least one gram per liter, e.g., polyethylene glycols/oxides), the influx of inflammatory cells is also minimized; this process is in contrast to conventional use of non-hydrogel or rigid, reservoir-based ocular implants. Moreover, certain proteins may be avoided to enhance biocompatibility; collagen or fibrin glues, for instance, tend to promote inflammation or unwanted cellular reactions since these releases signals as they are degraded that promote biological activity. Instead, synthetic materials are used, or peptidic sequences not normally found in nature. Moreover, the hydrogels may be made without external energy and/or without photoactivation so as to avoid heating or degradation of tissues, bearing in mind that the eye is a sensitive tissue. Additionally, biodegradable materials may be used so as to avoid a chronic foreign body reaction, e.g., as with thermally-formed gels that do not degrade. Further, soft materials or materials made in-situ to conform the shape of the surrounding tissues can minimize ocular distortion, and low-swelling materials may be used to eliminate vision-distortion caused by swelling. High pH materials may be avoided, both in the formation, introduction, or degradation phases.

Kits or Systems

Kits or systems for making hydrogels may be prepared. The kits are manufactured using medically acceptable conditions and contain precursors that have sterility, purity and preparation that is pharmaceutically acceptable. The kit may contain an applicator as appropriate, as well as instructions. A therapeutic agent may be included pre-mixed or available for mixing. Solvents/solutions may be provided in the kit or separately, or the components may be pre-mixed with the solvent. The kit may include syringes and/or needles for mixing and/or delivery.

In some embodiments, the kit has at least one precursor and an applicator. In some embodiments, a biodegradable, polymeric, synthetic hydrogel is formed by the reaction of an 8 armed 15,000 MW polyethylene glycol (PEG) having NHS-esters on each terminus of each arm with trilysine (which has primary amine nucleophiles) in phosphate or other buffer solutions. Visualization agents (e.g., FD&C Blue #1) may be incorporated into the sealant material.

In some embodiments the kit's applicator includes (or consists essentially of) syringes for syringe-to-syringe mixing. The delivery device is one of the syringes, and has a small bore tube with a LUER-lock on at least one end. After reconstitution of the product, an applicator tube is attached to the delivery syringe and the hydrogel is applied to the target tissue.

In some embodiments, kits having precursors and other materials as needed to form a hydrogel in situ with a therapeutic agent may be provided, with the component parts including those described herein. In some aspects, features of the hydrogels can thus be chosen to make hydrogels that are minimally swelling, delivered through a small needle, can be put into an aqueous low viscosity preparation to gel after placement. The hydrogel is not inflammatory or angiogenic, relies on biocompatible precursors, and is soft, hydrophilic, and conforming to the space wherein it is placed. The hydrogel may be easily removable or self-removing, and can be biodegradable or suited to delivery to easily accessible areas without dispersal. It can be made so it is easy to mix and use, with an option to combine all the precursors in a single container. The hydrogel may be made with safe, all-synthetic materials. The hydrogel formulations may be made to be adhesive to tissues. The degradation and/or delivery rate may be controlled to fit the time periods described. Since the hydrogel is cross-linked, it will not come out of the needle tract or other hole created for its delivery because it is shape-stable as deposited. The hydrogel depots have advantages relative to eye drops. Over 97% of topically administered eye drops are cleared via the tear ducts and do not end up penetrating the eye. Patient compliance may be enhanced by avoiding repeated dosing.

The use of fluent aqueous precursors to form a biodegradable drug depot allows for administration through small (e.g., 30 gauge) needles. Also, since the hydrogel can be made to not break down into acidic by products, the drug depots are well tolerated by sensitive tissues, such as the eye. Due to this, the implants can be made rather large in size (e.g., 1 ml capacity) relative to implants that are made from conventional biodegradable polymers, which are conventionally much smaller. Accordingly, some embodiments are hydrogels with volumes between about 0.5 to about 5 ml; artisans will immediately appreciate that all the ranges and values within the explicitly stated ranges are contemplated, e.g., 0.5 ml to about 1 ml. This makes such hydrogels eminently suited for periocular (episclereal or posterior subtenon injections (PST)) drug depots.

While some of the agent in one of the hydrogels or other crosslinked materials may be lost to the systemic circulation through a periocular route, a significantly larger implant size has the capability to retain therapeutic agent concentrations and accommodate larger implants to enable adequate transscleral diffusion of drugs across the sclera and into the back of the eye, bearing in mind that the human sclera surface area is about 17 cm$^2$. The hydrogels also help in localizing the drug; by way of contrast, if a drug suspension or microparticles are injected within the vitreous, they can migrate into the visual field and interfere with vision.

Example 1

Drug Incorporation into Hydrogel

Two precursors and a diluent were prepared. The first precursor was an 8-armed polyethylene glycol with a succinimidyl glutarate on the terminus of each arm, having a molecular weight of about 15,000. It was provided as a powder and blended with a dye (FD&A Blue) at a concentration of 0.11% w/w. The second precursor was trilysine in a 0.2 M sodium phosphate buffer at pH 8. A diluent for the first precursor was prepared to be 0.01 M sodium phosphate, pH 4.8.

A drug (as indicated in Examples below) was mixed into drug into diluent, and about 200 µl of the drug/diluent was drawn into a 1 ml syringe. 66 mg of the first precursor powder was placed into a separate 1 ml syringe. The two syringes were attached via a female-female luer connector, and the solution was injected back-and-forth until the powder was completely dissolved. The second precursor in its solution was drawn (200 µl) into a third syringe. With another female-female luer connector, the first and second precursors were thoroughly mixed. The mixed solution was drawn into one of the syringes and attached to a 4 inch length of silicone tubing that received the contents. After allowing a suitable reaction time, the tubing was cut into desired lengths, and the gel inside pushed out with a mandrel. Resulting hydrogel plugs were, in general, 0.125 inch in diameter and about 6.4 mm thick.

Unless otherwise indicated, the analysis of drug release profiles was ascertained using high-pressure liquid chromatography (HPLC). The disks were kept in a solution and the solution was periodically sampled and tested by HPLC to measure the concentration of drug in the solution. Total drug loading was determined by dissolving the disks in aqueous solution or in the presence of an alcohol such as octanol at high pH and measuring the drug content in the disks. Drug loading was 5% (weight of drug/total weight of hydrogel including contents) unless otherwise indicated.

Example 2

Release of Diclofenac Sodium

Figure 9:
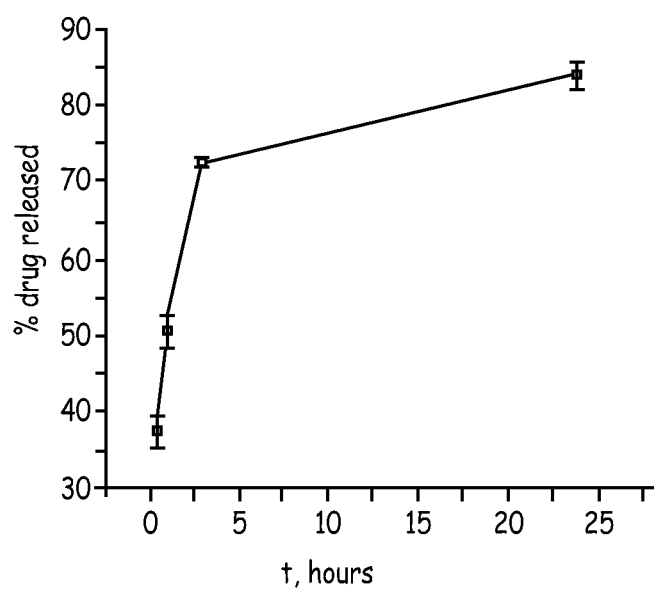
FIG. 9 depicts data gathered as per Example 2.

Diclofenac Sodium has a water solubility of about 1113 mg/L. It is an anti-inflammatory drug. It was loaded into a hydrogel as per Example 1 and was released as indicated in FIG. 9. Essentially complete release of the drug was observed in about 8 hours.

Example 3

Release of Bupivacaine

Figure 10:
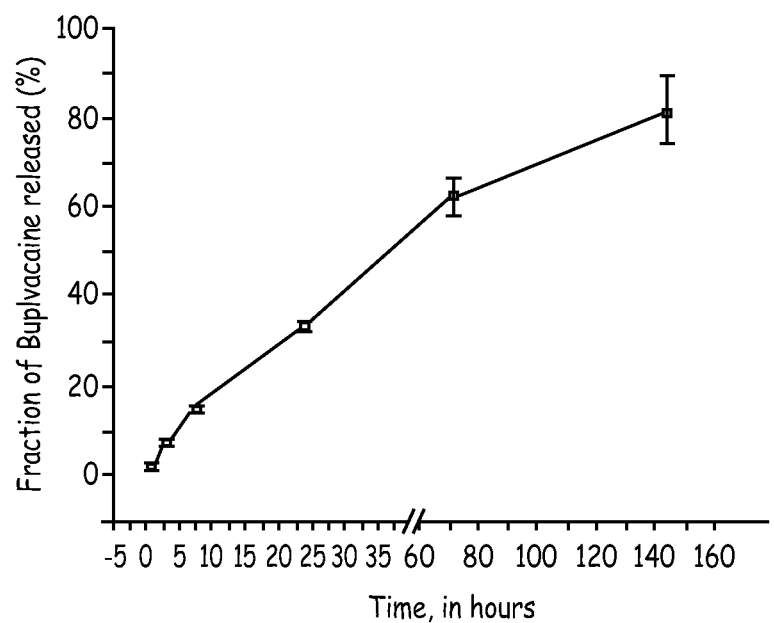
FIG. 10 depicts data gathered as per Example 3.

Bupivacaine has a water solubility of about 86 mg/L. It is a pain reliever that was converted from an HCl-salt to a free base to decrease water solubility. It was loaded into a hydrogel as per Example 1 and was released as indicated in FIG. 10. Sustained zero order release was observed over six days.

Example 4

Release of Nifedipine

Figure 11:
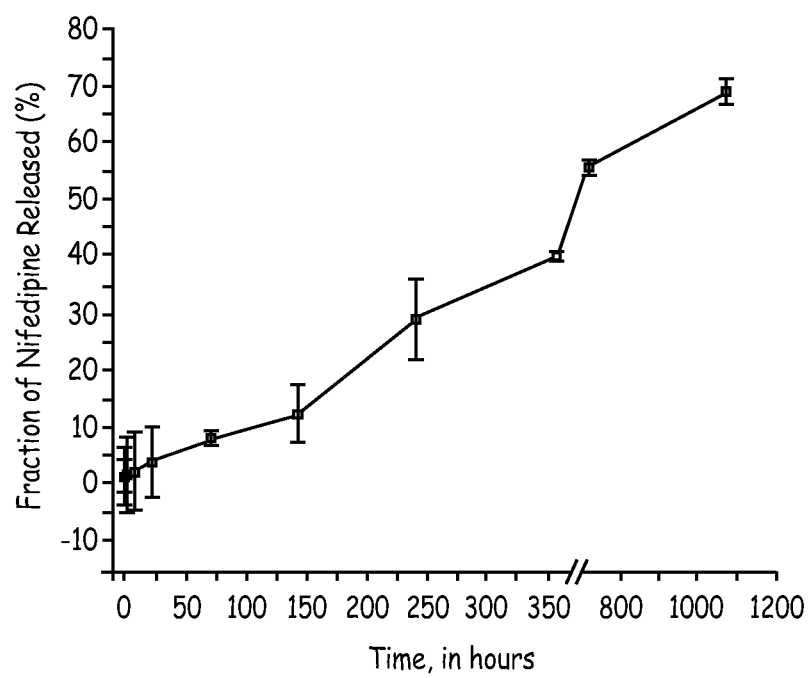
FIG. 11 depicts data gathered as per Example 4.

Nifedipine has a water solubility of less than 1 mg/L. It is a calcium channel blocker and Anti-hypertensive that relieves angina by increasing blood flow to the heart. It was loaded into a hydrogel as per Example 1 and was released as indicated in FIG. 11. Sustained zero order release over 45 days.

Example 5

Release of Ciprofloxacin

Figure 12:
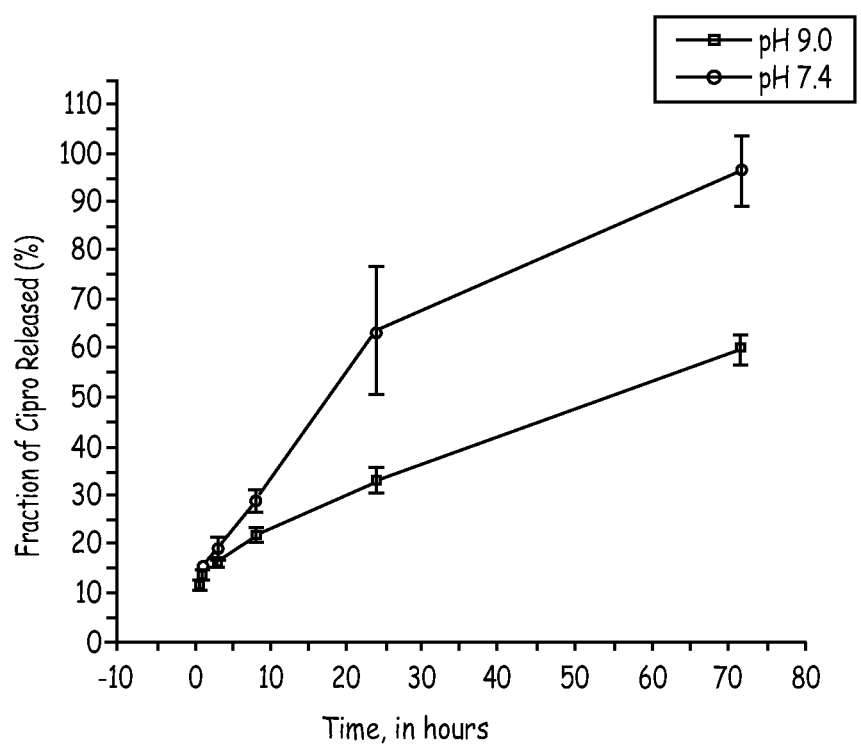
FIG. 12 depicts data gathered as per Example 5.

Ciprofloxacin has a water solubility of 160 mg/L. It is an antibiotic. It was loaded into a hydrogel as per Example 1 and was released as indicated in FIG. 12, which shows testes at ph 9.0 (squares) or pH 7.4 (circles). 50% of drug released by day three.

Example 6

Release of Mefenamic Acid

Figure 13:
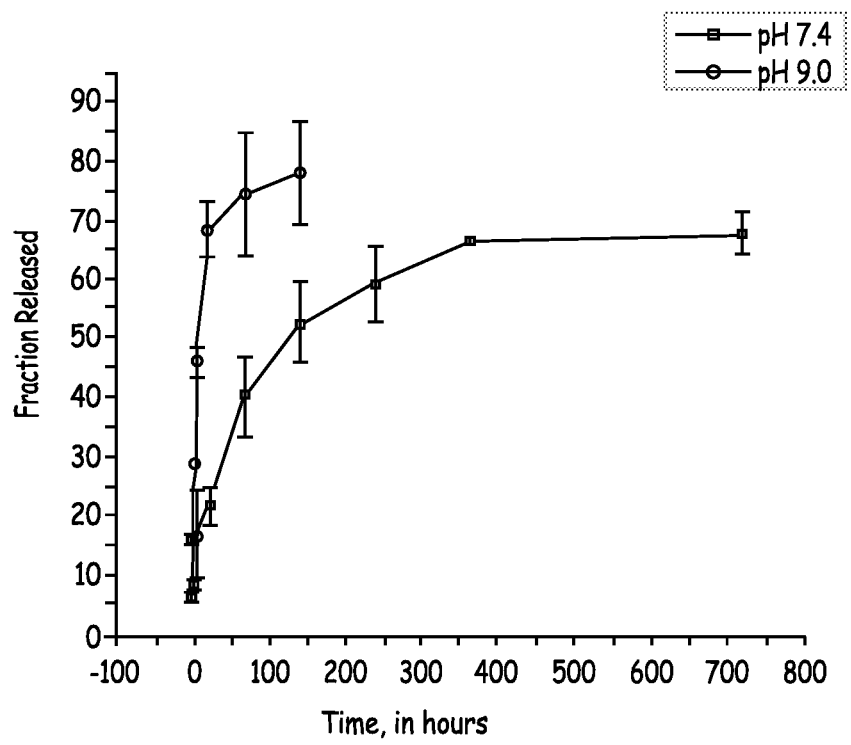
FIG. 13 depicts data gathered as per Example 6.

Mefenamic Acid is an NSAID for treating pain. It was loaded into a hydrogel as per Example 1 and was released as indicated in FIG. 13, which shows tests at ph 9.0 (squares) or pH 7.4 (circles). It was released over about 15 days although further degradation to its component parts at later times would release additional amounts of the drug.

Example 7

Release of Indomethacin

Figure 14:
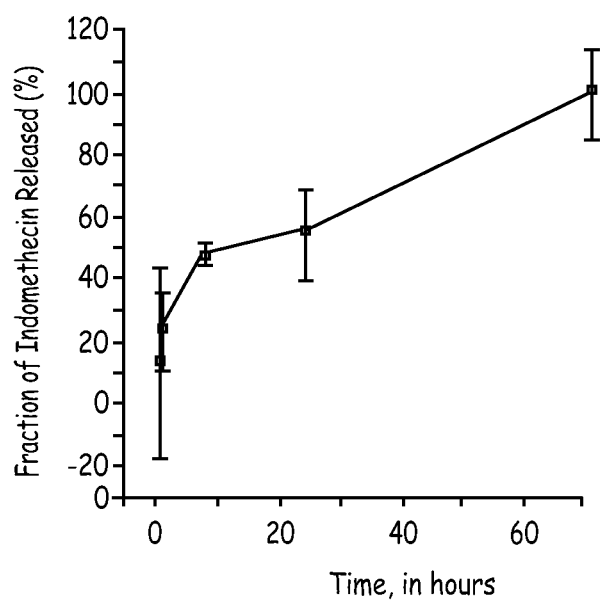
FIG. 14 depicts data gathered as per Example 7.

Indomethacin is another NSAID for treating pain. It was loaded into a hydrogel as per Example 1 and was released as indicated in FIG. 14, which shows tests at ph 9.0 (squares) or pH 7.4 (circles). The Figure shows the release profile over about six days; further release was observed but not quantified.

Example 8

Release of Triamcinolone

Figure 15:
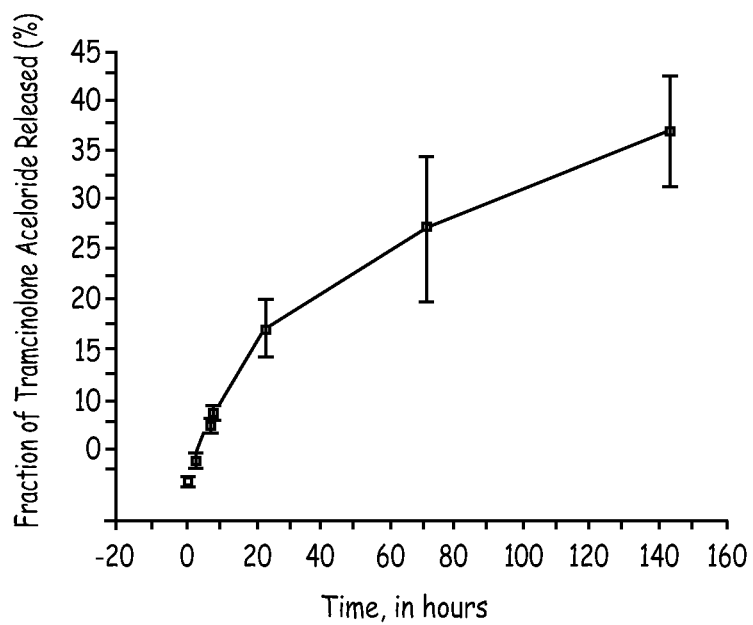
FIG. 15 depicts data gathered as per Example 8.

Triamcinolone has very little solubility in water and is a synthetic corticosteroid conventionally given orally, by injection, inhalation, or as a topical cream. It was loaded into a hydrogel as per Example 1 except that the loading was about 4% instead of 5%, and was released as indicated in FIG. 15, which shows tests up to about a week.

Example 9

Release of Dexamethasone

Figure 16:
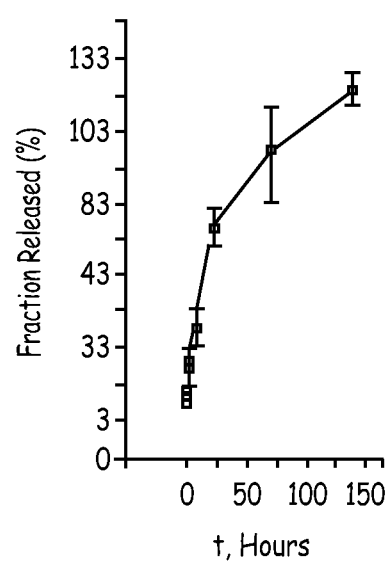
FIG. 16 depicts data gathered as per Example 9.

Dexamethasone is a glucocorticoid-type steroid hormone. It acts as an anti-inflammatory and immunosuppressant. It was loaded into a hydrogel as per Example 1 and was released as indicated in FIG. 16. The Figure shows the release profile over about six days; further release was observed but not quantified.

Many embodiments have been set forth herein. In general, components of the embodiments may be mixed-and-matched with each other as guided for the need to make functional embodiments.

The invention claimed is:

1. A method of treating an ophthalmic disease affecting an eye of a patient comprising forming a covalently-crosslinked hydrogel in situ at a site in an eye, wherein the hydrogel, when formed, has a volume of less than 0.5 ml and comprises a hydrophobic particle entrapped as a suspension within the hydrogel, the particle comprising a therapeutic agent that is released into the eye to treat the ophthalmic disease, wherein a time at which a cumulative 80% w/w of the therapeutic agent has been released is between about 14 and 120 days.

2. The method of claim 1 wherein the disease is a back-of-the eye disease.

3. The method of claim 2 wherein the back-of-the-eye disease is a selected from the group consisting of wet macular degeneration, dry macular degeneration, diabetic macular edema, cystoid macular edema, and diabetic retinopathy.

4. The method of claim 2 wherein the back-of-the-eye disease is an ocular disease of a posterior segment of the eye that affects a retina, macula or choroid, with said disease leading to a visual acuity disturbance, loss of sight, or blindness.

5. The method of claim 1 wherein the site is in a sclera of the eye.

6. The method of claim 1 wherein the site is substantially disposed between a sclera and a conjunctiva.

7. The method of claim 1 wherein the site is a potential space of the eye.

8. The method of claim 7 further comprising puncturing a conjunctiva to access the potential space.

9. The method of claim 7 comprising mechanically creating the potential space.

10. The method of claim 7 wherein the potential space is natural.

11. The method of claim 1 wherein the site is a vitreous of the eye or a posterior chamber of the eye.

12. The method of claim 1 wherein the hydrogel is low-swelling, as measurable by the hydrogel having a weight increasing no more than about 50% upon exposure to a physiological solution for twenty-four hours relative to a weight of the hydrogel at the time of formation.

13. The method of claim 1 wherein the hydrogel is water-degradable, as measurable by the hydrogel being dissolvable in vitro in an excess of water by degradation of water-degradable groups.

14. The method of claim 1 wherein the water-degradable groups are esters.

15. The method of claim 1 wherein the hydrogel is formed by combining a first synthetic precursor comprising nucleophilic groups with a second synthetic precursor comprising electrophilic groups to form covalent crosslinks by reaction of the nucleophilic groups with the electrophilic groups to form the biocompatible hydrogel.

16. The method of claim 15 further comprising injecting an aqueous mixture of the precursors to the site.

17. The method of claim 16 wherein the polymeric hydrophilic portions comprise poly(ethylene) glycol repeats.

18. The method of claim 1 wherein the hydrogel is formed by combining a first synthetic precursor with a second synthetic precursor.

19. The method of claim 1 wherein the therapeutic agent is selected from the group consisting of an inhibitor of vascular endothelial growth factor, a small molecule drug, and a protein.

20. The method of claim 1, wherein the therapeutic agent is an antiangiogenic agent.

21. The method of claim 20, wherein the antiangiogentic agent is an inhibitor of vascular endothelial growth factor.

* * * * *